US010016475B2

(12) United States Patent
Shon et al.

(10) Patent No.: US 10,016,475 B2
(45) Date of Patent: Jul. 10, 2018

(54) COMPOSITION FOR PREVENTING, IMPROVING, OR TREATING IMMUNE DISEASES COMPRISING NATURAL EXTRACTS AS ACTIVE INGREDIENTS

(71) Applicant: KOREA FOOD RESEARCH INSTITUTE, Gyeonggi-do (KR)

(72) Inventors: Dong-Hwa Shon, Gyeonggi-do (KR); Hee-Soon Shin, Gyeonggi-do (KR); Min-Jung Bae, Gyeonggi-do (KR); Ok-Hee Chai, Jeollabuk-do (KR); Chang-Yuil Kang, Seoul (KR); Dae-Woon Choi, Gangwon-do (KR); Gye-Young Choi, Busan (KR); Jeong-Hae Rho, Gyeonggi-do (KR); Jeong-Ryong Do, Gyeonggi-do (KR)

(73) Assignee: KOREA FOOD RESEARCH INSTITUTE, Gyeonggi-do (KR)

( * ) Notice: Subject to any disclaimer, the term of this patent is extended or adjusted under 35 U.S.C. 154(b) by 708 days.

(21) Appl. No.: 14/404,631

(22) PCT Filed: May 29, 2013

(86) PCT No.: PCT/KR2013/004717
§ 371 (c)(1),
(2) Date: Nov. 30, 2014

(87) PCT Pub. No.: WO2013/180469
PCT Pub. Date: Dec. 5, 2013

(65) Prior Publication Data
US 2015/0118266 A1    Apr. 30, 2015

(30) Foreign Application Priority Data

May 29, 2012  (KR) .................. 10-2012-0057005
May 29, 2012  (KR) .................. 10-2012-0057006
Dec. 6, 2012   (KR) .................. 10-2012-0141324
Dec. 6, 2012   (KR) .................. 10-2012-0141327
Dec. 6, 2012   (KR) .................. 10-2012-0141329

(51) Int. Cl.
| | | |
|---|---|---|
| *A01N 65/00* | (2009.01) | |
| *A61K 36/00* | (2006.01) | |
| *A61K 36/73* | (2006.01) | |
| *A61K 36/708* | (2006.01) | |
| *A61K 36/84* | (2006.01) | |
| *A61K 36/39* | (2006.01) | |
| *A61K 36/482* | (2006.01) | |
| *A61K 36/738* | (2006.01) | |
| *A61K 36/185* | (2006.01) | |
| *A61K 36/49* | (2006.01) | |
| *A61K 36/47* | (2006.01) | |
| *A61K 36/532* | (2006.01) | |
| *A23L 33/105* | (2016.01) | |

(52) U.S. Cl.
CPC .......... *A61K 36/708* (2013.01); *A23L 33/105* (2016.08); *A61K 36/185* (2013.01); *A61K 36/39* (2013.01); *A61K 36/47* (2013.01); *A61K 36/482* (2013.01); *A61K 36/49* (2013.01); *A61K 36/532* (2013.01); *A61K 36/738* (2013.01); *A61K 36/84* (2013.01); *A23V 2002/00* (2013.01)

(58) Field of Classification Search
None
See application file for complete search history.

(56) References Cited

FOREIGN PATENT DOCUMENTS

| KR | 10-2006-0118809 A | 11/2006 |
|---|---|---|
| KR | 10-2010-0105346 A | 9/2010 |
| KR | 10-2011-0032323 A | 3/2011 |
| KR | 10-2011-0098500 A | 9/2011 |

OTHER PUBLICATIONS

Zhang et a. 'Anti-inflammatory and analgesic effects of the ethanol extract of Rosa multiflora Thunb. hips.' J. Ethnophamacology 118:290-294, 2008.*
Guo et al. 'Anti-inflammatory activities and mechanisms of action of the petroleum ether fraction of Rosa multiflora Thunb. hips.' J. Ethnopharm acology 138:717-722, 2011.*
Lee, et al., (2007). "Meliae cortex extract exhibits anti-allergic activity through the inhibition of syk kinase in mast cells." *Toxicology and Applied Pharmacology.* 220:227-234.
Ko, et al., (2010). "Anti-inflammatory effects of pharbitis nil choisy in lipopolysaccharide-induceds raw 264.7 cells." *The Journal of Cosmetological Science.* 6(2):105-111.
Lee, et al., (2010). "Quercetin and kaempferol suppress immunoglobulin e-mediated allergic inflammation in rbl-2h3 and caco-2 cells." *Inflammation Research.* 59:847-854.

(Continued)

*Primary Examiner* — Nora Rooney
(74) *Attorney, Agent, or Firm* — Vorys, Sater, Seymour & Pease; Mih Suhn Koh

(57) ABSTRACT

The present invention provides a composition for preventing, improving, or treating Th1-mediated immune diseases or Th2-mediated immune diseases, an antihistamine composition, and an anti-inflammatory composition. The present invention provides a method for preventing, improving, or treating Th1-mediated immune diseases or Th2-mediated immune diseases, a method for inhibiting the release of histamine, and a method for preventing, improving, or treating inflammatory disorders. The composition according to the present invention has excellent inhibitory activities for IL-4 generation, the degranulation of mast cells, COX-2, 15-NOX, and the passing of allergens from through an intestinal epithelial cell layer, or an excellent Treg cell inducing activity. Further, the present invention provides a detailed mechanism of action of a natural substance and a food-drived antiallergenic substance, and provides stability, a reduction in production costs, and improved convenience of use by using a natural substance as a material.

3 Claims, 10 Drawing Sheets

(56) References Cited

OTHER PUBLICATIONS

O, et al., (2010). "Inhibitory effects of Nardostachys J atamansi on the maturation of dendritic cells." *The journal of Oriental Obsterics & Gynecology*. 23(3): 014-025.
Park, et al., (2010). "Isolation and identification of inhibitory compounds on helicobacter pylori from rosa multiflora thunberg fruit extracts." *Journal of Life Science*. 20(10):1511-1518.
Le, et al., (2012). "Effects of nardostachys jatamansi on atopic dermatitis-like skin lesions." *J Korean Orient Pediatr*. 26(2):13-24.
International Search Report for PCT/KR2013/004717.
Kim, Young Sook et al., "Inhibitory Effect ofKIOM-79, a New Herbal Prescription, on AGEs Formation and Expressions of Type 4 Collagen and TGF-1 in STZ-induced Diabetic Rats", Korean Journal of Pharmacognosy, 2006, vol. 37, No. 2, pp. 103-109.
Title of publication—Bahat Nighantu Ratnakara (Saligramanighantubhusanam) Page(s) being submitted—06(p. 04-09) ( Ref.pg. No. of publication: 48 ) Publication Date—1997 Publisher—Khemaraja Srikrsnadas Prakasana Place of Publication—Mumbai-4, India.†
Author, Mohammad Azam Khan Title of publication—Muheet-e-Azam vol. III (19th century AD) Page(s) being submitted—05 (p. 10-14) ( Ref.pg. No. of publication:58 ) Publication Date—1887 AD Publisher—Matba Nizami Place of Publication—Kanpur, India.†
Title of publication—Ayurveda Sarasamgrahah—Page(s) being submitted—05 (p. 15-19) ( Ref.pg. No. of publication:299 ) Publication Date—Edn. 2003 Publisher—Shri Baidyanath Ayurveda Bhavan Limited Place of Publication—Calcutta, India.†

\* cited by examiner
† cited by third party

COMPOSITION FOR PREVENTING, IMPROVING, OR TREATING IMMUNE DISEASES COMPRISING NATURAL EXTRACTS AS ACTIVE INGREDIENTS

CROSS REFERENCE TO RELATED APPLICATIONS AND CLAIM OF PRIORITY

This patent application is a National Phase application under 35 U.S.C. § 371 of International Application No. PCT/KR2013/004717, filed 29 May 2013, which claims priority to Korean Patent Application No. 10-2012-0057005 filed in the Korean Intellectual Property Office on May 29, 2012, Korean Patent Application No. 10-2012-0057006 filed in the Korean Intellectual Property Office on May 29, 2012, Korean Patent Application No. 10-2012-0141324 filed in the Korean Intellectual Property Office on Dec. 6, 2012, Korean Patent Application No. 10-2012-0141327 filed in the Korean Intellectual Property Office on Dec. 6, 2012, and Korean Patent Application No. 10-2012-0141329 filed in the Korean Intellectual Property Office on Dec. 6, 2012, entire contents of which are incorporated herein by reference.

This invention has been achieved as a result of Project #E0121500 with the support of the Korean Ministry of Knowledge Economy. The research and management agency for this assignment is Korea Food Research Institute, and the research business is named "Major Business of Korea Food Research Institute". The name of the assignment is "Research and Development of Functional Foods against Allergies" and the supervising organization is Korea Food Research Institute while the duration of research is from 2012 Jan. 1 to 2012 Jan. 31.

BACKGROUND

1. Field of Invention

The present invention relates to a composition for preventing, improving, or treating Th1-mediated immune diseases or Th2-mediated immune diseases comprising one or more extracts as active ingredients selected from kaladana (*Pharbitis* nil Choisy), cassia seeds (*Senna obtusifolia* L.), spurge (*Euphorbia pekinensis*), spikenard (*Nardostachys jatamanse*), wrinkled giant hyssop (*Agastache rugosa*), roots of Phytolaccaceae (*Phytolacca esculenta*), inner skin of *Castanea crenata* (*Castanea crenata* S.), white pharbitis seeds (*Pharbitis* nil Chois), fruits of *Rosa multiflora* (*Rosa multiflora*) and rhubarbs (*Rheum rhabarbarum* L.); and a method for preventing, improving, or treating histamine-mediated diseases 2. Background Art In recent years, allergies have increased due to various reason including changing dietary habits, better hygiene and intensified pollution along with advancement in income levels, and about 20-25% of the entire population have symptoms of, for example, atopic dermatitis (AD), asthma and rhinitis. These significantly affect the quality of life, and may lead to serious social issues. Also, it cannot be ignored that food allergies are found in 6-8% of infants and also cause 35% of children's ADs.

Until now, a medicine that shows definite effects against various allergies has not existed and, thus, treating children who have these allergies has been especially difficult even though children's ADs have been on the rise. Particularly, drugs that have similar characteristics as steroids bring about serious side effects so there are currently attempts around the world to prepare for alternative solutions. To combat these allergies, materials that are expected to have positive results without any toxicity or side effects must be extracted from natural substances and foods, which then should be actively utilized. Moreover, the anti-allergy mechanism of action for active materials and their components must be also examined in detail.

The main-stream medicine popular in the 21st century have been those for allergies and diabetes (Japan's Nikkei Sankyo Newspapers). In the United States, around 50 million people possess many different kinds of allergies (drug and medicine market, $5.2 billion annually). In Japan, there exists a market for functional foods worth around 60 billion JPY while that of drugs and medicine related to allergies is worth 156 billion JPY annually, compared to the Korean market for drugs and medicine, which is worth around 50 billion KRW. Looking at the recent trend of patents in functional foods, most of the ones submitted are in the area of "anti-obesity", followed by "anti-allergy", an area that is anticipated to be of much added value but also requires necessary preparation.

There has been an increasing need for development of health functional foods, emphasizing immune function controls or activation of allergy suppression, which has resulted in numerous patents submitted to the Korea Food and Drug Administration. Also, according to patent analyses in Japan during recent years, the future potential for functional foods was reported to lie in the activation of "anti-obesity" and then "anti-allergy".

The term "allergy" has been originated from a Greek word "allos", which means "hypersensitive reaction", and refers to the "deformed". In other words, an allergy is an occurrence caused by a substance, which has no effect on average people, inducing abnormally hypersensitive reaction such as hives, itching, nasal discharges and/or coughs on a particular individual due to malfunctioning of the immune system. In the last 20 years, the incidence rate of allergic diseases has been trending upward globally (1, 2). Primary reasons for this increase include more time spent indoors, development of new materials, sudden influx of allergy-inducing materials particularly from overseas, unstable immune statuses due to environmental contamination and stress, and changing dietary habits. Although the incidence rate of allergic diseases in the people of modern era has steadily increased, many only rely on well-known treatments such as antihistamines or steroids without finding a fundamental treat for it (3).

Gell and Coombes (1963) traditionally divide allergic reactions into 4 categories based on time and types of manifestation (4). Types I through III are humoral immunologic responses (immediate-type) in which antibodies are involved while Type IV is a cellular immunologic response (delayed-type). Also, based on the types of cells and medium concerned with immune reactions, responses are divided into immediate or early responses in which symptoms are displayed within minutes, and late-stage responses in which symptoms appear after a few hours. For example, Type I takes the form of an immediate hypersensitive reaction while Type IV is a delayed hypersensitive reaction. Most allergic reactions are categorized as Type I, which includes diseases such as asthma, rhinitis, conjunctivitis, food and drug allergies and atopic dermatitis, and severe cases lead to anaphylaxis, which may risk one's life.

Type I immediate hypersensitive reactions are further divided into 2 steps. In the first step, allergen penetrates into a body and suppresses secretion of IgE and IgG1. Once the balance between Th1 cellular response, which produces IL-12 and IFN-r that increase secretion of IgG2a, and Th2 cellular response, which produces IL-4, IL-5 and IL-13, tips in the direction of Th2, IL-4, IL-13 and others are discharged due to an excessive hypersensitive reaction of Th2. Because of this effect, IgE specific antibodies produced by B cells are attached to mast cells or basophils, and, subsequently, an allergic crisis is ready, all of which is called the sensitization of allergens (5-7) (Refer to figure: "Allergic Diseases", "Th1/Th2 Balance").

The second step of allergic crisis is divided into early and late responses. In the early response, an allergen re-penetrates the body, stimulates mast cells and induces degranulative reactions, releasing histamines, lipid metabolites and Cytokine at this time to cause blood vessels to expand. In the late response, neutrophils, eosinophils, macrophage, Th2 cells and basophils infiltrate into a particular tissue and are activated, which leads to inflammation and symptoms of atopic dermatitis, rhinitis and asthma (7). Among these secreted matters of degranulation, histamine is the most well-known and used as an essential indicator for allergic symptoms due to its relations to immediate hypersensitive reactions (8).

On the other hand, food allergies have occurred in about 3 to 6% of children in developed countries for the past 10 years and show an upward trend (9). Food allergies, which are caused by food coming into a body through the digestive tract, belong primarily to Type I hypersensitive reaction. For allergy patients, food allergens penetrate through intestinal canals at an undigested state (4, 10) and, thus, the absorption of allergens inside intestines is the first step of an allergic crisis (11). Intestinal canals not only take care of digestion and absorption of nutrients but also are involved in various biomodulation. Primary characteristics of intestinal epithelial cells include digestion and absorption, the role as a barrier and transfer and conversion of food signals. As they also possess developed a special immune system (mucosal immunity) and nerve tissues, the role of digestive and intestinal canals must not be underestimated. Thus, as a barrier, intestinal epithelial cells restrict the penetration of large molecules by a tight junction; however, if the tight junction is damaged, the permeability increases due to the dysfunction of the barrier, which may result in diseases such as food allergies, celiac disease and acute pancreatitis (12-17). In other words, food allergies can be prevented by strengthening the barrier function of intestinal canals through stabilization of tight junction.

The research papers previously mentioned have reported, to a great extent, about the activation of the allergy inhibition in foods and natural products, which have been popularly used especially by Koreans in oriental medicine and home remedies to treat and prevent allergies (18, 19). These research mostly evaluate the activation of degranulation inhibition in medicinal herbs such as areca nuts, Anemarrhena rhizome and fenugreek (20-33) and also report on Th1/Th2 immune response controls in polysaccharide components such as quercetin, Siberian gooseberries, garlic, perilla oil, konjac, lobulus and liriope rhizome in addition to those in Lingzhi mushrooms and Japanese soy sauce as well as royal jelly and cordyceps (34-44). Also reported were results on the activation which suppresses allergic inflammation in lactobacillus, fermented barley and cheonggukjang, a Korean fermented soybean soup (45-49).

Throughout the entire specification, many papers and patent documents are referenced and their citations are represented. The disclosures of cited papers and patent documents are entirely incorporated by reference into the present specification, and the level of the technical field within which the present invention falls and details of the present invention are explained more clearly.

SUMMARY

The present inventors have endeavored to develop natural products that may prevent or treat diseases and symptoms caused by Th1 or Th2 immune responses such as inflammatory diseases or allergies. As a result, the inventors have successfully completed this research by finding out that extracts of kaladana (*Pharbitis* nil Choisy), cassia seeds (*Senna obtusifolia* L.), spurge (*Euphorbia pekinensis*), spikenard (*Nardostachys jatamanse*), wrinkled giant hyssop (*Agastache rugosa*), roots of Phytolaccaceae (*Phytolacca esculenta*), inner skin of *Castanea crenata* (*Castanea crenata* S.), white pharbitis seeds (*Pharbitis* nil Chois), fruits of *Rosa multiflora* (*Rosa multiflora*) and rhubarbs (*Rheum rhabarbarum* L.) suppress both production of IL-4 and degranulation of mast cells, activate inhibition of COX-2, 15-NOX and allergens' penetration into epithelial cells, and induce their differentiation into Treg cells.

Accordingly, an aspect of the present invention is to provide a composition for preventing, improving, or treating Th1-mediated immune diseases or Th2-mediated immune diseases.

Another aspect of the present invention is to provide an anti-histamine composition.

Still another aspect of the present invention is to provide a anti-inflammatory composition.

Still another aspect of the present invention is to provide a method for preventing, improving, or treating Th1-mediated immune diseases or Th2-mediated immune diseases.

Still another aspect of the present invention is to provide a method for preventing, improving, or treating histamine-mediated diseases.

Still another aspect of the present invention is to provide a method for preventing, improving, or treating an inflammation.

Other purposes and advantages of the present invention will become clarified by the following detailed description of invention, claims, and drawings.

DETAILED DESCRIPTION

Figure 1:
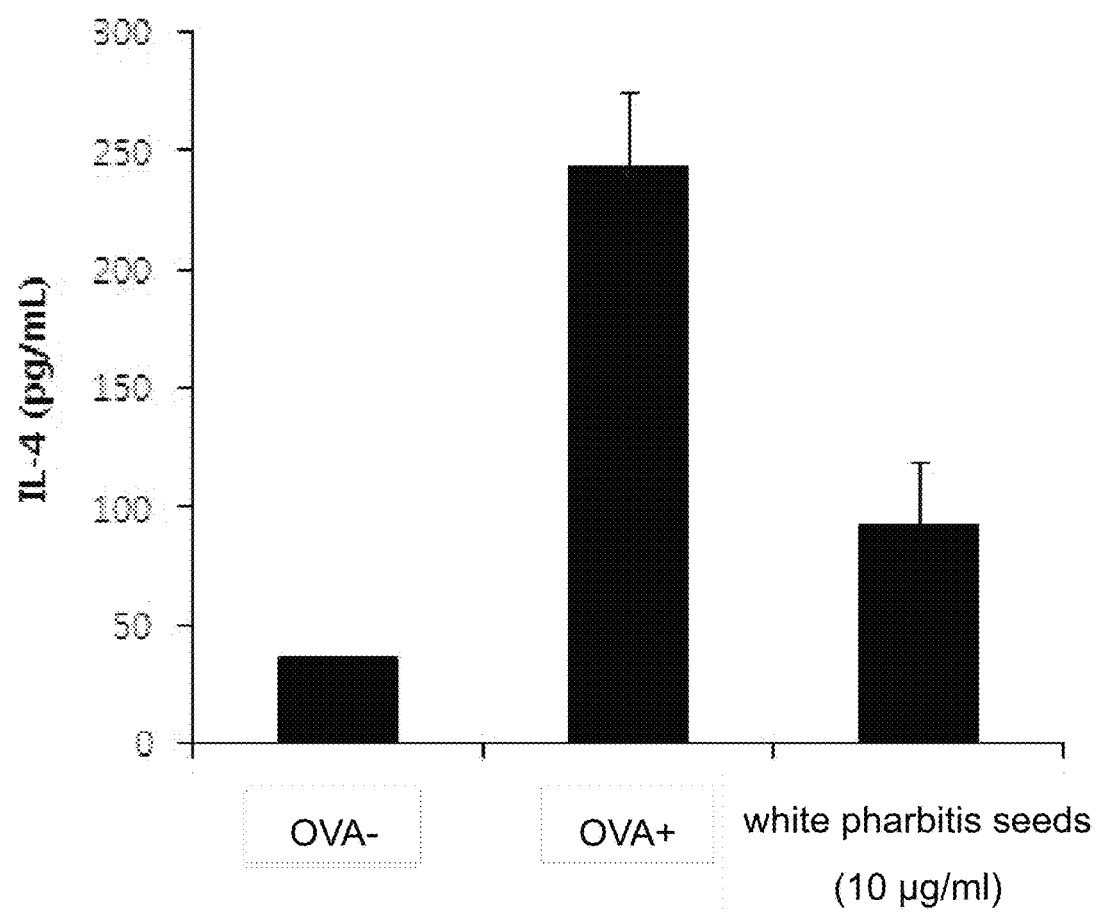
FIG. 1 displays the effect of white pharbitis seed extracts in releasing IL-4 of mouse splenocytes.

In accordance with an aspect of the present invention, there is provided a composition for preventing, improving, or treating Th1-mediated immune diseases or Th2-mediated immune diseases comprising one or more extracts as active ingredients selected from kaladana (*Pharbitis* nil Choisy), cassia seeds (*Senna obtusifolia* L.), spurge (*Euphorbia pekinensis*), spikenard (*Nardostachys jatamanse*), wrinkled giant hyssop (*Agastache rugosa*), roots of Phytolaccaceae (*Phytolacca esculenta*), inner skin of *Castanea crenata* (*Castanea crenata* S.), white pharbitis seeds (*Pharbitis* nil Chois), fruits of *Rosa multiflora* (*Rosa multiflora*) and rhubarbs (*Rheum rhabarbarum* L.).

Another aspect of the present invention is to provide a method for preventing, improving, or treating Th1-mediated immune diseases or Th2-mediated immune diseases comprising a step for administrating the composition comprising one or more extracts as active ingredients selected from kaladana (*Pharbitis* nil Choisy), cassia seeds (*Senna obtusifolia* L.), spurge (*Euphorbia pekinensis*), spikenard (*Nardostachys jatamanse*), wrinkled giant hyssop (*Agastache rugosa*), roots of Phytolaccaceae (*Phytolacca esculenta*), inner skin of *Castanea crenata* (*Castanea crenata* S.), white pharbitis seeds (*Pharbitis* nil Chois), fruits of *Rosa multiflora* (*Rosa multiflora*) and rhubarbs (*Rheum rhabarbarum* L.).

The present inventors have endeavored to develop natural products that may prevent or treat diseases and symptoms caused by Th1 or Th2 immune responses such as inflammatory diseases or allergies. As a result, the inventors have successfully completed this research by finding out that extracts of kaladana (*Pharbitis* nil Choisy), cassia seeds (*Senna obtusifolia* L.), spurge (*Euphorbia pekinensis*), spikenard (*Nardostachys jatamanse*), wrinkled giant hyssop (*Agastache rugosa*), roots of Phytolaccaceae (*Phytolacca esculenta*), inner skin of *Castanea crenata* (*Castanea crenata* S.), white pharbitis seeds (*Pharbitis* nil Chois), fruits of *Rosa multiflora* (*Rosa multiflora*) and rhubarbs (*Rheum rhabarbarum* L.) suppress both production of IL-4 and degranulation of mast cells, activate inhibition of COX-2, 15-NOX and allergens' penetration into epithelial cells, and induce their differentiation into Treg cells.

The extracts of kaladana (*Pharbitis* nil Choisy), cassia seeds (*Senna obtusifolia* L.), spurge (*Euphorbia pekinensis*), spikenard (*Nardostachys jatamanse*), wrinkled giant hyssop (*Agastache rugosa*), roots of Phytolaccaceae (*Phytolacca esculenta*), inner skin of *Castanea crenata* (*Castanea crenata* S.), white pharbitis seeds (*Pharbitis* nil Chois), fruits of *Rosa multiflora* (*Rosa multiflora*) and rhubarbs (*Rheum rhabarbarum* L.) can be obtained by using various extraction solvents. According to an embodiment of the present invention, the extract solvents are polar solvents or non-polar solvents. The polar solvents include (i) water, (ii) alcohols (preferably, methanol, ethanol, propanol, butanol, normal propanol, iso-propanol, normal butanol, 1-pentanol, 2-butoxy ethanol or ethylene glycol), (iii) acetic acid, (iv) DMFO (dimethyl-formamide) and (v) DMSO (dimethyl sulfoxide). The non-polar solvents include acetone, acetonitrile, ethyl acetate, methyl acetate, fluoroalkanes, pentan, hexan, 2,2,4-trimethylpentan, trimethylpentan, decans, cyclohexan, cyclopentan, diisobutylene, 1-pentene, 1-chlorobutan, 1-chloropentan, o-xylene, diisopropyl ether, 2-chlorobutan, toluene, 1-chloropropan, chlorobenzene, benzene, diethyl ether, diethyl sulfide, chloroform, dichloromethane, 1,2-dichloroethane, aniline, diethylamine, ether, CCl4 and THF (tetrahydrofuran).

The extraction solvents used in this invention are (a) water, (b) anhydrides of carbon number 1 through 4 or enhydrous alcohol with a low number of molecules (methanol, ethanol, propanol, butanol, etc.), (c) mixed solvents of the aforementioned alcohol and water, (d) acetone, (e) ethyl acetate, (f) chloroform, (g) butyl acetate, (h) 1,3-butylene glycol, (i) hexane and (j) diethyl ether. Also, the extracts of this invention are obtained by applying water, ethanol or the combination to kaladana, cassia seeds, spurge, wrinkled giant hyssop, roots of Phytolaccaceae, inner skin of *Castanea crenata*, white pharbitis seeds, *Rosa multiflora*, *Nardostachys jatamanse* or rhubarbs.

The term used herein "extract" is widely used to mean crude extracts, while a wider meaning also refers to additional materials fractionated from these extracts. That is, the extracts of kaladana, cassia seeds, spurge, wrinkled giant hyssop, roots of Phytolaccaceae, inner skin of *Castanea crenata*, white pharbitis seeds, *Rosa multiflora*, *Nardostachys jatamanse* or rhubarbs include, in definition, not only the extraction solvents previously explained but also any extracts acquired by applying an additional refinement process. For instance, there is fractionation obtained by penetrating the above extracts through an ultrafilter that retains constant cut-off values for the number of molecules; another example is the differentiation based on various chromatographies (those manufactured for differentiation by size, electric charge, hydrophobicity or hydrophilicity). Also, these fractionation, which has been acquired by many different refinement procedures carried out additionally, are included in the extracts of kaladana, cassia seeds, spurge, wrinkled giant hyssop, roots of Phytolaccaceae, inner skin of *Castanea crenata*, white pharbitis seeds, *Rosa multiflora*, *Nardostachys jatamanse* or rhubarbs.

These extracts can be manufactured in a powdery state through an additional process consisted of vacuum distillation, freeze-drying or spray drying.

The term used herein "comprising as active ingredients" refers to the case in which a sufficient amount of extracts are contained in order to maximize their effects or achieve activation. This invention is a composition of the extracts from natural plant materials including kaladana, cassia seeds, spurge, wrinkled giant hyssop, roots of Phytolaccaceae, inner skin of *Castanea crenata*, white pharbitis seeds, *Rosa multiflora*, *Nardostachys jatamanse* or rhubarbs, which leaves no side effects in a human body even when too much of it is administered. Therefore, the person in the art may determine the maximum quantity of these extracts within a proper range.

The composition of this invention may be used to prevent or treat various Th2-mediated immunity diseases, disorders or symptoms.

The term used herein "Th2-mediated immunity diseases" refer to the diseases involved with IgE and mast cells based on production and activation of allergen-specific Th2 cells.

The term used herein "Th2 cells" represents the subset of helper T cell lymphocytes specified for the purposes of gene manifestation, protein secretion and functional activation. Th2 cells manifest a pattern of IL-4, IL-5, IL-10 and IL-13 Cytokines, and are involved in humoral immunity reactions.

There are no specific restrictions on the Th2-mediated immunity diseases and, according to an embodiment of the present invention, this type of Th2-induced immunity diseases is allergic diseases.

The term used herein "allergy" means various diseases and symptoms induced by a human immune system's hypersensitive reactions against a certain matter coming from outside. Allergic diseases that apply to the compositions of this invention are, desirably, Type I immediate hypersensitive reactions and Type IV delayed hypersensitive reactions. Type immediate hypersensitive reactions include bronchial asthma, allergic rhinitis, atopic dermatitis, allergic conjunctivitis, allergic otitis media, hives and anaphylactic shocks, whereas some of the Type IV delayed hypersensitive reactions are contact hypersensitivity, allergic contact dermatitis, bacteria allergies, fungus allergies, virus allergies, and drug allergies, thyroiditis and allergic encephalitis. Type immediate hypersensitive reactions are divided into 2 steps. In the first step, allergen penetrates into a body and suppresses secretion of IgE and IgG1. Once the balance between Th1 cellular response, which produces IL-12 and IFN-r that increase secretion of IgG2a, and Th2 cellular response, which produces IL-4, IL-5 and IL-13, tips in the direction of Th2, IL-4, IL-13 and others are discharged due to an excessive hypersensitive reaction of Th2. Because of this effect, IgE specific antibodies produced by B cells are attached to mast cells or basophils, and, subsequently, an allergic crisis is ready, all of which is called the sensitization of allergens. The second step of allergic crisis is divided into early and late responses. In the early response, an allergen re-penetrates the body, stimulates mast cells and induces degranulative reactions, releasing histamines, lipid metabolites and Cytokine at this time to cause blood vessels to expand. In the late response, neutrophils, eosinophils, macrophage, Th2 cells and basophils infiltrate into a particular tissue and are activated, which leads to inflammation and symptoms of atopic dermatitis, rhinitis and asthma. Among these secreted matters of degranulation, histamine is the most well-known and used as an essential indicator for allergic symptoms due to its relations to immediate hypersensitive reactions.

The allergic diseases to which the invented compositions are applied include atopic dermatitis, other dermal diseases related to atopic syndrome, allergic rhinitis (acute or chronic), hay fever, asthma and food allergies, but not limited thereto. According to an embodiment of the present invention, the allergic diseases to which this invention is applied include asthma, allergic rhinitis, allergic dermatitis, allergic atopic dermatitis or food allergies.

According to an specific embodiment of the present invention, the allergic diseases are food allergies.

A major characteristic of the invention is that the compositions retain a state of activation to suppress Th2 immune responses.

According to an embodiment of the present invention, the compositions inhibit the production of IL-4.

According to other embodiment of the present invention, compositions that comprise kaladana extracts as active ingredients reduce the production of IL-4 by 10-99%, 30-99%, 50-99%, 70-99%, 80-99% or 90-99%, compared to a control group. According to other embodiment of the present invention, the compositions of this invention have $IC_{50}$ values of 5-10, 6-9 or 7-8 µg/ml for the production of IL-4. According to other embodiment of the present invention, the kaladana extracts have concentration of around 50-100, 70-90 or 75-85 mg/ml.

According to other embodiment of the present invention, compositions that comprise rhubarb extracts as active ingredients reduce the production of IL-4 by 10-99%, 30-99%, 50-99%, 70-99%, 70-90% or 75-85%, compared to a control group. According to other embodiment of the present invention, the rhubarb extracts have concentration of around 50-100, 70-90 or 75-85 mg/ml.

According to other embodiment of the present invention, compositions that comprise wrinkled giant hyssop extracts as active ingredients reduce the production of IL-4 by 10-99%, 30-99%, 50-99%, 50-90%, 60-80% or 65-75%, compared to a control group. According to other embodiment of the present invention, the compositions of this invention have $IC_{50}$ values of 10-50, 20-40 or 25-35 µg/ml for the production of IL-4. According to other embodiment of the present invention, the wrinkled giant hyssop extracts have concentration of around 50-100, 70-90 or 75-85 mg/ml.

According to other embodiment of the present invention, compositions that comprise roots of Phytolaccaceae extracts as active ingredients reduce the production of IL-4 by 10-80%, 30-80%, 30-70%, 40-70% or 50-65%, compared to a control group. According to other embodiment of the present invention, the compositions of this invention have $IC_{50}$ values of 0.5-5, 0.5-3 or 1-3 µg/ml for the production of IL-4. According to other embodiment of the present invention, the roots of Phytolaccaceae extracts have concentration of around 50-100, 70-90 or 75-85 mg/ml.

According to other embodiment of the present invention, compositions that comprise spurge extracts as active ingredients reduce the production of IL-4 by 10-60%, 10-50%, 10-40%, 20-40% or 25-35%, compared to a control group. According to other embodiment of the present invention, the spurge extracts have concentration of around 50-100, 70-90 or 75-85 mg/ml.

According to other embodiment of the present invention, compositions that comprise inner skin of *Castanea crenata* extracts as active ingredients reduce the production of IL-4 by 10-50%, 20-50%, 20-40% or 25-35%, compared to a control group. According to other embodiment of the present invention, the inner skin of *Castanea crenata* extracts have concentration of around 50-100, 70-90 or 75-85 mg/ml.

According to other embodiment of the present invention, compositions that comprise white pharbitis seeds extracts as active ingredients reduce the production of IL-4 by 10-70%, 30-70%, 50-70% or 55-65%, compared to a control group. According to other embodiment of the present invention, the white pharbitis seeds extracts have concentration of around 1-30, 5-30, 7-30, 7-20 or 7-15 µg/ml.

According to other embodiment of the present invention, compositions that comprise *Rosa multiflora* extracts as active ingredients reduce the production of IL-4 by 10-50%, 20-50% or 20-40%, compared to a control group. According to other embodiment of the present invention, the *Rosa multiflora* extracts have concentration of around 1-50, 5-50, 10-50, 20-50, 20-40 or 25-35 µg/ml.

According to other embodiment of the present invention, compositions that comprise spikenard extracts as active ingredients reduce the production of IL-4 by 10-50%, 20-50% or 30-40%, compared to a control group. According to other embodiment of the present invention, the spikenard extracts have concentration of around 1-50, 5-50, 10-50, 20-50, 20-40 or 25-35 µg/ml.

According to an embodiment of the present invention, the compositions of the invention inhibit degranulation.

The term used herein "degranulation" refers to a process in which antibacterial cytotoxic molecules are separated from granules and secretory vesicles existing inside a specific cell, which includes granulocytes (neutrophils, eosinophils and basophils) and mast cells inside the immune system as well as specific lymph cells such as natural killer cells and cytotoxic T cells.

As shown in Examples below, compositions of this invention have been proven to be activated for degranulation inhibition of mast cells through observing the inhibition of histamine secretion, β-hexosaminidase release and mast cells deformations.

According to other embodiment of the present invention, compositions comprising kaladana extracts as active ingredients suppress the degranulation of mast cells by 30-90%, compared to a control group. According to other embodiment of the present invention, the compositions comprising kaladana extracts as active ingredients suppress the secretion of histamines by 50-90%, 70-90% or 75-85%. According to other embodiment of the present invention, the compositions comprising kaladana extracts as active ingredients suppress the release of R-hexosaminidase by 30-70%, 30-60% or 40-50%. According to other embodiment of the present invention, the compositions comprising kaladana extracts as active ingredients have concentration of 30-150, 50-150, 70-150, 90-150, 90-120 or 95-105 mg/ml.

According to other embodiment of the present invention, compositions comprising cassia seeds extracts as active ingredients suppress the degranulation of mast cells by 10-60%, compared to a control group. According to other embodiment of the present invention, the compositions comprising cassia seeds extracts as active ingredients suppress the secretion of histamines by 10-50%, 10-40% or 20-30%. According to other embodiment of the present invention, the compositions comprising cassia seeds extracts as active ingredients suppress the release of β-hexosaminidase by 10-50%, 20-50% or 30-45%. According to other embodiment of the present invention, the compositions comprising cassia seeds extracts as active ingredients have concentration of 1-20, 3-20, 3-10 or 3-7 μl/ml.

According to other embodiment of the present invention, compositions comprising rhubarbs extracts as active ingredients suppress the degranulation of mast cells by 10-50%, compared to a control group. According to other embodiment of the present invention, the compositions comprising rhubarbs extracts as active ingredients suppress the secretion of histamines by 20-40% or 25-35%. According to other embodiment of the present invention, the compositions comprising rhubarbs extracts as active ingredients suppress the release of β-hexosaminidase by 10-30% or 15-20%. According to other embodiment of the present invention, the compositions comprising rhubarbs extracts as active ingredients have concentration of 1-20, 3-20, 3-10 or 3-7 μl/ml.

According to other embodiment of the present invention, compositions comprising wrinkled giant hyssop extracts as active ingredients suppress the degranulation of mast cells by 10-50%, compared to a control group. According to other embodiment of the present invention, the compositions comprising wrinkled giant hyssop extracts as active ingredients suppress the secretion of histamines by 20-50% or 30-45%. According to other embodiment of the present invention, the compositions comprising wrinkled giant hyssop extracts as active ingredients suppress the release of β-hexosaminidase by 10-40% or 25-40%. According to other embodiment of the present invention, the compositions comprising wrinkled giant hyssop extracts as active ingredients have concentration of 1-20, 3-20, 3-10 or 3-7 μl/ml.

According to other embodiment of the present invention, compositions comprising roots of Phytolaccaceae extracts as active ingredients suppress the degranulation of mast cells by 10-90%, compared to a control group. According to other embodiment of the present invention, the compositions comprising roots of Phytolaccaceae extracts as active ingredients suppress the secretion of histamines by 30-90%, 50-90% or 60-80%. According to other embodiment of the present invention, the compositions comprising roots of Phytolaccaceae extracts as active ingredients suppress the release of β-hexosaminidase by 10-70%, 30-70% or 40-60%. According to other embodiment of the present invention, the compositions comprising roots of Phytolaccaceae extracts as active ingredients have concentration of 1-20, 3-20, 3-10 or 3-7 μl/ml.

According to other embodiment of the present invention, compositions comprising spurge extracts as active ingredients suppress the degranulation of mast cells by 10-70%, compared to a control group. According to other embodiment of the present invention, the compositions comprising spurge extracts as active ingredients suppress the secretion of histamines by 30-70% or 40-60%. According to other embodiment of the present invention, the compositions comprising spurge extracts as active ingredients suppress the release of β-hexosaminidase by 30-70%, 40-60% or 40-50%. According to other embodiment of the present invention, the compositions comprising spurge extracts as active ingredients have concentration of 1-20, 3-20, 3-10 or 3-7 μl/ml.

According to other embodiment of the present invention, compositions comprising inner skin of *Castanea crenata* extracts as active ingredients suppress the degranulation of mast cells by 10-60%, compared to a control group. According to other embodiment of the present invention, the compositions comprising inner skin of *Castanea crenata* extracts as active ingredients suppress the secretion of histamines by 10-50%, 20-50% or 30-40%. According to other embodiment of the present invention, the compositions comprising inner skin of *Castanea crenata* extracts as active ingredients suppress the release of β-hexosaminidase by 10-50%, 10-40% or 20-30%. According to other embodiment of the present invention, the compositions comprising inner skin of *Castanea crenata* extracts as active ingredients have concentration of 1-20, 3-20, 3-10 or 3-7 μl/ml.

According to other embodiment of the present invention, compositions comprising white pharbitis seeds extracts as active ingredients suppress the degranulation of mast cells by 10-80%, 30-70% or 40-60%, compared to a control group. According to other embodiment of the present invention, the compositions comprising inner white pharbitis seeds extracts as active ingredients have concentration of 0.001-10, 0.005-10, 0.01-10, 0.01-5, 0.01-3 or 0.01-1 μg/ml.

According to other embodiment of the present invention, compositions comprising *Rosa multiflora* extracts as active ingredients suppress the degranulation of mast cells by 10-90%, 20-90% or 20-85%, compared to a control group. According to other embodiment of the present invention, the compositions having concentration of 0.05-1.0, 0.05-0.5, 0.05-0.3 or 0.05-0.1 suppress the degranulation by 10-30% or 20-25%. According to other embodiment of the present invention, the compositions having concentration of 0.1-10, 0.5-10, 0.5-5, 0.5-3, 0.7-3 or 0.7-2 suppress the degranulation by 30-90%, 50-90% or 70-90%.

According to other embodiment of the present invention, compositions comprising spikenard extracts as active ingredients suppress the degranulation of mast cells by 10-80%, 30-70% or 40-70%, compared to a control group. According to other embodiment of the present invention, the compositions comprising spikenard extracts as active ingredients have concentration of 0.001-10, 0.005-10, 0.01-10, 0.01-5, 0.01-3 or 0.01-1 μg/ml.

The composition of this invention may be used to prevent or treat various Th1-mediated immunity diseases, disorders and symptoms.

The term used herein "Th1-mediated immunity diseases" refers to the diseases involved with Cytokines, like IL-13, IL-2, IL-12, IL-17, IFN-γ or TNF-α, which are created by the formation and/or activation of Th1 cells.

The term used herein "Th1 cells" represents the subset of helper T cell lymphocytes specified for the purposes of gene manifestation, protein secretion and functional activation. Th1 cells manifest a Cytokine pattern, which synthesizes IL-2 and IFN-γ but does not synthesize IL-4, IL-5, IL-10 and IL-13. Also, the cells are involved in cell-mediated immune responses on various pathogens within cells, organ-specific autoimmune diseases as well as delayed hypersensitive reactions.

There are no specific restrictions on the Th1-mediated immunity diseases and the types of Th1-induced immunity diseases, to which the compositions of the invention are applied, are transplant rejection, autoimmune diseases or inflammatory diseases. Also considered as Th1-induced immunity diseases include colitis, inflammatory bowel disease, Type I diabetes, Type II diabetes, rheumatoid arthritis, reactive arthritis, osteoarthritis, psoriasis, scleroderma, osteoporosis, atherosclerosis, myocarditis, endocarditis, pericarditis, cystic fibrosis, Hashimoto's thyroiditis, Graves' disease, leprosy, syphilis, Lyme disease, borreliosis, neurogenic borreliosis, tuberculosis, sarcoidosis, lupus, discoid lupus, chilblain lupus, lupus nephritis, systemic lupus erythematosus, asthma, macular degeneration, uveitis, irritable bowel syndrome, Crohn's disease, Sjogren's syndrome, fibromyalgia, chronic fatigue syndrome, chronic fatigue & immunological incompetence syndrome, myalgic encephalomyelitis, amyotrophic lateral sclerosis, Parkinson's disease, multiple sclerosis, autism spectrum disorder, attention deficit disorder and attention deficit & hyperactivity disorder, but are not limited thereto. The types of Th1-induced immunity diseases, to which the compositions of the invention are applied, are colitis, inflammatory bowel disease and rheumatoid arthritis.

According to an embodiment of the present invention, compositions that comprise extracts of kaladana, cassia seeds, spurges, inner skin of *Castanea crenata* or rhubarbs as active ingredients retain an inhibitive function for COX-2 (cyclooxygenase-2) activation.

According to other embodiment of the present invention, the kaladana extracts of this invention have concentration of 60-100, 70-90 or 75-85 mg/ml.

According to other embodiment of the present invention, for COX-2 $IC_{50}$ and COX-1 $IC_{50}$, cassia seed extracts have values within the range of 2.5-4.0, spurge extracts in the range of 2.5-4.5, rhubarb extracts in the range of 7.0-9.0 while those of *Castanea crenata* are between 7.5 and 9.5.

Cassia seed extracts of this invention have COX-2 $IC_{50}$ values of 100-250, 150-250, 150-200 or 180-200 µg/ml while those of spurges have corresponding values of 10-40, 25-40 or 35-45 µg/ml. Lastly, the extracts of *Castanea crenata* have COX-2 $IC_{50}$ values of 10-40, 20-40 or 30-40 µg/ml.

According to an embodiment of the present invention, the compositions that comprising extracts of spurges or roots of Phytolaccaceae as active ingredients inhibit the activation of 15-LOX (15-Lipooxygenase).

Moreover, spurge extracts of the invention have 15-LOX IC50 values of 70-100, 80-93 or 85-90 µg/ml while those of Phytolaccaceae have corresponding values of 80-120, 90-110 or 95-105 µg/ml.

On the other hand, the compositions that contain extracts of *Nardostachys jatamanse* as active ingredients induce the differentiation into Treg cells. The transformation from T cell to Treg cell can be seen from the increasing manifestation of Foxp3, and this induction of Treg cells brings about the balance between Th1 and Th2 and is effective in preventing, improving or curing Th1- and/or Th2-mediated immune diseases.

If the extracts of *Nardostachys jatamanse* are processed using 1-20, 3-20 or 3-15 µg/ml, compositions that contain these extracts increase the manifestation of Fox3p by 1.5-4 times, compared to a control group. Moreover, if the extracts of are processed using 5-20, 7-20, 7-15 or 7-13 µg/ml, the compositions increase the manifestation of Fox3p by 3-4 times, compared to a control group.

According to still another aspect of the present invention, the present invention provides an anti-histamine composition comprising one or more extracts as active ingredients selected from kaladana (*Pharbitis* nil Choisy), cassia seeds (*Senna obtusifolia* L.), spurge (*Euphorbia pekinensis*), wrinkled giant hyssop (*Agastache rugosa*), roots of Phytolaccaceae (*Phytolacca esculenta*), inner skin of *Castanea crenata* (*Castanea crenata* S.) and rhubarbs (*Rheum rhabarbarum* L.).

According to still another aspect of the present invention, the present invention provides a method for inhibiting the release of histamine comprising a step for administrating the composition of the invention to a subject.

According to still another aspect of the present invention, the present invention provides a method for preventing, improving or treating histamine-mediated diseases comprising a step for administrating an anti-histamine composition comprising one or more extracts as active ingredients selected from kaladana (*Pharbitis* nil Choisy), cassia seeds (*Senna obtusifolia* L.), spurge (*Euphorbia pekinensis*), wrinkled giant hyssop (*Agastache rugosa*), roots of Phytolaccaceae (*Phytolacca esculenta*), inner skin of *Castanea crenata* (*Castanea crenata* S.) and rhubarbs (*Rheum rhabarbarum* L.).

The term used herein "histamine-mediated disease" refers to the disease caused by histamine being secreted from a mast cell. The histamine-mediated diseases to which anti-histamine compositions of this invention are applied include chronic urticaria, angioedema, asthma and symptoms similar to allergies.

According to still another aspect of the present invention, the present invention provides an anti-inflammatory composition comprising one or more extracts as active ingredients selected from kaladana (*Pharbitis* nil Choisy), cassia seeds (*Senna obtusifolia* L.), spurge (*Euphorbia pekinensis*), wrinkled giant hyssop (*Agastache rugosa*), roots of Phytolaccaceae (*Phytolacca esculenta*), inner skin of *Castanea crenata* (*Castanea crenata* S.) and rhubarbs (*Rheum rhabarbarum* L.).

According to still another aspect of the present invention, the present invention provides a method for preventing, improving or treating inflammatory diseases comprising a step for administrating an anti-histamine composition comprising one or more extracts as active ingredients selected from kaladana (*Pharbitis* nil Choisy), cassia seeds (*Senna obtusifolia* L.), spurge (*Euphorbia pekinensis*), wrinkled giant hyssop (*Agastache rugosa*), roots of Phytolaccaceae (*Phytolacca esculenta*), inner skin of *Castanea crenata* (*Castanea crenata* S.) and rhubarbs (*Rheum rhabarbarum* L.).

The inflammatory diseases applied to the anti-inflammatory compositions of this invention are both acute and chronic inflammatory diseases including, but not limited to, inflammatory skin disease (for example, eczema and psoriasis), rheumatoid arthritis, contact dermatitis, acne, paranasal sinusitis, osteoarthritis, gastritis, gout, urarthritis, ulcer, chronic bronchitis, acute lung damage, inflammatory lung disease, inflammatory bowel disease (for example, Crohn's disease and ulcerative colitis), ankylosing spondylitis, sepsis, septic shock, angiitis, and bursitis.

According to an embodiment of the present invention, the compositions that comprise extracts of cassia seeds, *Rosa multiflora* or their combination as active ingredients prevent Th1- or Th2-mediated immune diseases.

According to other embodiment of the present invention, the compositions that comprise these extracts as active ingredients suppress the penetration of allergens into epithelium, which refers to the layer of epithelial cells.

Cassia seed extracts of this invention inhibit allergens' penetration into epithelium by 10-99, 30-99%, 50-99%, 70-99% or 90-99%, compared to the control group.

*Rosa multiflora* extracts of this invention inhibit allergens' penetration into epithelium by 10-50%, 20-50% or 30-40%, compared to the control group.

Compositions for preventing, improving, or treating Th1-mediated immune diseases or Th2-mediated immune diseases, anti-histamine, anti-inflammatory comprising one or more extracts as active ingredients selected from kaladana (*Pharbitis* nil Choisy), cassia seeds (*Senna obtusifolia* L.), spurge (*Euphorbia pekinensis*), spikenard (*Nardostachys jatamanse*), wrinkled giant hyssop (*Agastache rugosa*), roots of Phytolaccaceae (*Phytolacca esculenta*), inner skin of *Castanea crenata* (*Castanea crenata* S.), white pharbitis seeds (*Pharbitis* nil Chois), fruits of *Rosa multiflora* (*Rosa multiflora*) and rhubarbs (*Rheum rhabarbarum* L.) are pharmaceutical, food, functional food, cosmetic or fodder compositions.

Compositions of this invention can be manufactured as pharmaceutical.

In a proper application, they are pharmaceutical compositions that contain (a) pharmaceutically effective doses of one or more extracts selected among kaladana, cassia seeds, spurge, wrinkled giant hyssop, roots of Phytolaccaceae, inner skin of *Castanea crenata*, white pharbitis seeds, *Rosa multiflora, Nardostachys jatamanse* or rhubarbs, and (b) pharmaceutically accepted carriers. In this specification, the term "pharmaceutically effective dose" refers to a sufficient amount needed to achieve effectiveness or activation of one or more extracts selected from the above group of natural products.

If the compositions of this invention are manufactured as pharmaceutical compositions, they can include pharmaceutically accepted carriers. These carriers, which are normally used in manufactured medicine, include, but are not limited to, lactose, dextrose, sucrose, Sorbitol, Mannitol, starch, acacia rubber, calcium phosphate, alginate, gelatin, calcium silicate, microcrystalline cellulose, polyvinyl pyrrolidone, cellulose, water, syrup, methyl cellulose, methyl hydroxybenzoate, profile hydroxybenzoate, talc, stearic acid magnesium and mineral oil. Also included in pharmaceutical compositions are lubricants, humectants, sweetening agents, cordials, emulsifiers, suspensions and preservatives. Proper carriers and medication pharmaceutically accepted are written in detail in Remington's Pharmaceutical Sciences (19th ed., 1995).

The pharmaceutical compositions of this invention may be administered by either orally or non-orally; in this application, an oral administration is performed.

The appropriate dosage of the pharmaceutical composition of the present invention is varied depending on factors, such as the method of formulation, the manner of administration, the age, body weight, sex, morbidity, and diet of the patient, the time of administration, the route of administration, the rate of excretion, and response sensitivity. According to the present invention, the appropriate dosage per day is 0.001-100 mg/kg (body weight).

The pharmaceutical composition of the present invention may be formulated into a unit dosage form or may be formulated by being contained in a multi-dose container, using a pharmaceutically acceptable carrier and/or excipient, according to the method easily performed by person having ordinary skills in the art to which the present invention pertains. Here, the dosage form may be a solution in an oily or aqueous medium, a suspension, a syrup, or an emulsion, or an extract, a powder, a granule, a tablet, or a capsule, and may further include a dispersant or a stabilizer.

Compositions of this invention can be manufactured as a food composition. If the compositions of this invention are manufactured as compositions for preventing, improving, or treating Th1-mediated immune diseases or Th2-mediated immune diseases, anti-histamine compositions or anti-inflammatory compositions, they can include additional ingredients which are used in food manufacturing, such as proteins, carbohydrates, lipids, nutrients, seasonings and flavours. Carbohydrates include monosaccharides such as glucose, fructose etc.; disaccharides such as maltose, sucrose, oligosaccharides, etc.; and polysaccharides such as dextrin, cyclodextrin as a normal saccharides and xylitol, sorbitol, erythritol as a sugar alcohol. When these compositions are manufactured as food compositions, ingredients normally added during food manufacturing are included while both natural (thaumatin and stevia extracts (for example, rebaudioside A, glycyrrhizin, etc.)) and synthetic (saccharin, aspartame, etc.) cordials may be used, on top of the aforementioned natural products. Moreover, if the food compositions of this invention are manufactured as tonics, the following can be added on top of the aforementioned natural products: citric acid, high fructose corn syrup, sugar, glucose, acetic acid, malic acid, fruit juice, eucommia bark extracts, jujube extracts and licorice extracts.

Compositions of this invention can be manufactured as a functional food composition. If the compositions of this invention are manufactured as functional food compositions, ingredients normally added during food manufacturing such as protein, carbohydrate, fat, nutrients and flavoring agents are included.

For example, the natural carbohydrates include monosaccharides (e.g. glucose, fructose); disaccharides (e.g. maltose, sucrose); oligosaccharides; poly saccharides (e.g. dextrin, cyclodextrin); and saccharide alcohols (e.g. xylitol, sorbitol, erythritol. Flavoring agents include natural flavoring agents (e.g. taumarin, stevia extracts) and synthetic flavoring agents (e.g. sacarine, aspartam).

Compositions of this invention can be manufactured as a cosmetic composition. In addition to antihistamine and anti-inflammatory compositions, there are those, for the purposes of prevention, improvement or curing of Th1- or Th2-mediated immune diseases, that comprising one or more extracts selected from kaladana, cassia seeds, spurge, wrinkled giant hyssop, roots of Phytolaccaceae, inner skin of *Castanea crenata*, white pharbitis seeds, *Rosa multiflora, Nardostachys jatamanse* or rhubarbs. When these compositions are manufactured as cosmetic compositions, ingredients and adjurvants normally added in cosmetic compositions such as stabilizers, solubilizers, vitamins, pigments and perfumes as well as carriers are included, in addition to the aforementioned natural products.

The cosmetic compositions of the present invention are manufactured into various formulations such as solutions, suspensions, emulsions, pastes, gels, creams, lotions, powders, soaps, surfactant-containing cleansing, oils, powdery foundations, emulsion foundations, wax foundations and sprays, but is not limited thereto. More detailed, emollient toilet water, nourishment water, nourishment creams, massage creams, essences, eye creams, cleansing creams, cleansing foams, cleansing water, packs, sprays or powders.

The pastes, creams or gels formulations may include animal oils, plant oils, waxes, paraffin, starch, tragacanth, cellulose derivates, polyethylene glycol, silicon, bentonite, silica, talc or zinc oxide as carriers.

The powder or spray formulations may include lactose, talc, silica, aluminum hydroxide, calcium silicate or polyamide powder as carriers, especially, the spray formulation may additionally include propellants such as chlorofluorohydrocarbon, propan/butan or dimethyl ether.

The solution or emulsion formulations may include solvents or emulsifying agents as carriers such as water, ethanol, isopropanol, ethyl carbonate, ethyl acetate, benzyl alcohol, benzyl benzoate, propylene glycol, 1,3-butylglycol oil, glycerol aliphatic ester, polyethylene glycol or fatty acid ester of sorbitan.

If the type of this invention is a suspension, the following may be used as a carrier ingredient: diluting agents such as water, ethanol and propylene glycol, suspensions such as ethoxylated isostearyl alcohol, polyoxyethylene sorbitol ester and polyoxyethylene sorbitan ester, microcrystalline cellulose, aluminum metal hydroxides, bentonite, agar and tragacanth.

If the type of this invention is a surfactant-containing cleansing, it can include aliphatic alcohol sulfate, aliphatic alcohol ether sulfate, sulfosuccinate monoester, isethionate, imidazolium derivates, methyl taurate, sarcosinate, fatty acid amide ether sulfate, alkylamidobetaine, aliphatic alcohols, fatty acid glyceride, fatty acid diethanolamide, plant oils, lanolin derivates or ethoxyfying glycerol fatty acid ester as carriers.

Compositions of this invention can be manufactured as a fodder composition.

The fodder composition can additionally include kaladana (*Pharbitis* nil Choisy), cassia seeds (*Senna obtusifolia* L.), spurge (*Euphorbia pekinensis*), spikenard (*Nardostachys jatamanse*), wrinkled giant hyssop (*Agastache rugosa*), roots of Phytolaccaceae (*Phytolacca esculenta*), inner skin of *Castanea crenata* (*Castanea crenata* S.), white pharbitis seeds (*Pharbitis* nil Chois), fruits of *Rosa multiflora* (*Rosa multiflora*) and rhubarbs (*Rheum rhabarbarum* L.) as raw materials, or additionally include additives such as vitamins, amino acids, minerals, antioxidants, antibiotics, antimicrobial agents or other additives. The additives can be powders, granules, pellets or suspensions.

If the compositions of this invention are manufactured as fodder compositions, they can be supplied either independently or as a mixture with fodder for both land and sea animals. In this case, the types of fodder include, but are not limited to, powder food, solid food, moist pellet food, dry pellet food, EP (Extruder Pellet) food and raw food.

Features and advantages of the present invention are summarized as follows:

(a) The present invention relates to compositions for preventing, improving, or treating Th1-mediated immune diseases or Th2-mediated immune diseases, anti-histamine compositions and anti-inflammatory compositions.

(b) This invention provides methods for preventing, improving, or treating Th1-mediated immune diseases or Th2-mediated immune diseases, and inflammatory diseases, in addition to suppressing secretion of histamine.

(c) The compositions of this invention have excellent capabilities of activating inhibition of IL-4 production, degranulation of mast cells, COX-2, 15-NOX and allergens' penetration into the epithelial cells layer as well as of activating induction of Treg cells.

(d) This invention provides detailed mechanism of action for anti-allergy materials in natural products and foods.

(e) This invention uses natural products for its materials in order to provide stability, reduction in manufacturing costs and convenience of usage.

Hereinafter, the present invention will be described in detail with reference to examples. These examples are only for illustrating the present invention more specifically, and it will be apparent to those skilled in the art that the scope of the present invention is not limited by these examples.

EXAMPLES

Example

Methods & Materials

Reagent and Equipment

General reagents such as OVA (Ovalbumin) and ELISA (Enzyme-linked immunosorbent assay) use products manufactured by Sigma (St. Louis, Mo., U.S.A.). For Millicell-ERS (Electrical Resistance System) used to measure TEER (transepithelial electrical resistance, $\Omega/cm^2$), a product from Millipore Corporation (Bedford, Mass., U.S.A.) is utilized. For anti-OVA antibodies as well as mixtures of specific antibodies and enzymes for ELISA, a product manufactured internally is used (Juhyun, Ryu, Chunwook, Park, Jongmi, Lee, Donghwa, Son. Antigenicity Changes of Ovomucoid and Ovalbumin in Chicken Egg White by NaOH, Heat and Protease Treatments. Korean Journal of Food Science and Technology. 36(1): 147-151. 2004) while a Nunc product is used for microplates, a Molecular Devices product for readers, and BD Bioscience (San Diego, Calif., U.S.A.) product for ELISA kits used to measure IgE and Cytokine.

Preparing Samples and Solvent Extracts kaladana (*Pharbitis* nil Choisy), cassia seeds (*Senna obtusifolia* L.), spurge (*Euphorbia pekinensis*), wrinkled giant hyssop (*Agastache rugosa*), roots of Phytolaccaceae (*Phytolacca esculenta*), inner skin of *Castanea crenata* (*Castanea crenata* S.) and rhubarbs (*Rheum rhabarbarum* L.) that had been purchased in the market were used for this process. To manufacture extracts of the above natural products, samples were first pulverized and added with 25 times of 50% EtOH. Then, by using Soxwave 100 (Fontenay-Sous-Bois, France), a microwave extraction system from BDH Prolabo, the solution was subject to microwave processing at 90 W for 5 minutes and extracted. The extract was filtered through a filter paper, vacuum-concentrated to about 40%, and membrane-filtered with a 0.45-µm syringe filter before maintaining it constantly at 4° C. and putting to use.

That is, 1,000 ml of 70% EtOH was added to a 100 g extract of kaladana, cassia seeds, spurge, wrinkled giant hyssop, roots of Phytolaccaceae, inner skin of *Castanea crenata* and rhubarbs, and then extracted via the method of reflux (performed twice). After 3 hours of reflux at 60° C., the extract was collected once, a step which was performed one more time after 1,000 ml of 70% EtOH was added to it, resulting in 2 total extract collections. Then, with a rotary evaporator, the extract was maintained in a freezer and used after vacuum concentration to a final amount of about 100 ml as well as freeze drying.

White pharbitis seeds, *Rosa multiflora* and *Nardostachys jatamanse* were purchased from Korea Plant Extract Bank and used as samples, each of which was extracted with 95% ethanol or water.

Testing of Th1/Th2 Cytokine Balance Control Activated by Extracts (Ex Vivo)

Mouse Spleen Cell Culture Immunized with OVA—Extracts of Kaladana, Cassia Seeds, Spurge, Wrinkled Giant Hyssop, Roots of Phytolaccaceae, Inner Skin of *Castanea crenata* and Rhubarbs Allergens were administered to 6-year-old female BALB/c mice twice in the span of a week through intraperitoneal immunization in order to induce allergies. The allergens, a solution of OVA (20 μg) and alum (2 mg) mixed for 30 minutes, were introperitoneally injected for 100 μl on each mouse (n=5). After a week of immunization, the cervical vertebrae of the mice were dislocated, their spleens were extracted under sterile conditions, and the basal medium of 1 ml (RPMI1640 containing 2-mercaptoethanol and antibiotics) was moved to a small petri dish and subsequently kept on top of an ice box. The spleens contained in a petri dish, were monocellularized first by using a mesh and cleaned twice with 5 ml of basal medium before performing a centrifugation at 1000 rpm for 10 minutes. After removing the supernatant, 1 ml of RBC (Red Blood Cell) buffer solution (Sigma, U.S.A.) was added, shaken sufficiently by hand and suspended. It was then left on ice for 3 minutes and another 10 ml of basal medium was added and suspended before performing 2 times of centrifugation at 1000 rpm for 10 minutes. After removing the supernatant, a basal medium with 10% FBS was added and suspended, and a cell suspension was manufactured by diluting 10 μl, out of 50 μl, with 90 μl of saline, resulting in a solution diluted by 10 times. Then, 190 μl of saline and 190 μl of trypan blue (Sigma, U.S.A.) were added to and mixed with this diluted cell suspension and left for 5 minutes, after which the number of cells was measured. Antigens (100 μg/ml) were processed on a 48-well plate and 4 μg/ml for each of the aforementioned natural products were added. Then, the spleen cells were separately deposited on the well at 5×106 cells, 500 μl and concentration of the well, respectively. The supernatant was collected after 72 hours of incubation in a thermal hygrostat with 37, $CO_2$.

Mouse Spleen Cell Culture Immunized with OVA—White Pharbitis Seeds, *Rosa multiflora* and *Nardostachys jatamanse*

Allergens were administered to 5-year-old female BALB/c mice twice in the span of a week through intraperitoneal immunization in order to induce allergies. The allergens, a solution of OVA (20 μg) and alum (2 mg) mixed for 30 minutes, were introperitoneally injected for 100 μl on each mouse (n=5). After a week of immunization, the cervical vertebrae of the mice were dislocated, their spleens were extracted under sterile conditions, and the basal medium of 1 ml (RPMI1640 containing 2-mercaptoethanol and antibiotics, WelGene, Daegu, Korea) was moved to a small petri dish and subsequently kept on top of an ice box. The spleens contained in a petri dish, were monocellularized first by using a mesh and cleaned twice with 5 ml of basal medium before performing a centrifugation at 1500 rpm for 5 minutes. After removing the supernatant, 1 ml of RBC (Red Blood Cell) buffer solution (Sigma R7757, U.S.A.) was added, shaken sufficiently by hand and suspended. It was then left on ice for 3 minutes and another 10 ml of basal medium was added and suspended before performing 2 times of centrifugation at 1500 rpm for 5 minutes. Antigens (OVA, 100 μg/ml) were processed on a 96-well plate and 10 μg/ml of white pharbitis seeds, *rosa multiflora* and *nardostachys jatamanse* extracts, which had been prepared in advance, were added. Then, the concentration of the spleen cells were processed at 5×106 cells/well, and, lastly, the supernatant was collected after 72 hours of incubation in a thermal hygrostat with 37° C. $CO_2$.

Analyzing Cytokine of Spleen Cell Culture Supernatant (Activating Inhibition of IL-4 Production)—Extracts of Kaladana, Cassia Seeds, Spurge, Wrinkled Giant Hyssop, Roots of Phytolaccaceae, Inner Skin of *Castanea crenata* and Rhubarbs The secretion types of Cytokine, which are revealed as the extracts of kaladana, cassia seeds, spurge, wrinkled giant hyssop, roots of Phytolaccaceae, inner skin of *Castanea crenata* and rhubarbs are added to the aforementioned spleen cells, were examined. The analysis was performed by using an ELISA kit (BD Bioscience) according to the protocol of the manufacturer. To explain simply, captured antibodies were added onto 96 well plates, which were placed at 4 for one night. The 96 well plates coated with the captured antibodies were then cleaned 3 times with a cleansing buffer (PBS containing Tween 20, PBST), and 200 μl of PBS, which contains 10% FBS, was added to each well before undergoing blocking for 1 hour at room temperature. After 3 times of cleansing, 100 μl of each standard specimen and extract of the natural products was deposited onto each well and left to react for 2 hours at room temperature. After cleaning 5 more times, 100 μl of each detection antibody and streptavidin-HRP was deposited onto each well and left to react for 1 hour at room temperature. After another 7 times of cleaning, each well was driven to develop a certain color, with the help of 100 μl of substrate solution (citric acid-phosphate buffer containing 0.01% TMB, pH 5.0, 0.001% H202), for 30 minutes at room temperature. Then, 50 μl of 2M H2S04 was added to each well in order to stop the color reaction. The level of color formation was gauged with THERMOmax, a microplate reader (Molecular Devices, U.S.A.) by measuring the absorbance at 450 nm.

Analyzing Cytokine of Spleen Cell Culture Supernatant (Activating Inhibition of IL-4 Production)—White Pharbitis Seeds, *Rosa multiflora* and *Nardostachys jatamanse*

Spleen cell culture supernatants in which the antigens (OVA, 100 μg/ml) as well as 10 μg/ml of white pharbitis seeds, *rosa multiflora* and *nardostachys jatamanse* extracts are processed were collected after 72 hours and used in IL-4 analyses. For the Cytokine analysis, BD OptEIA™ MOUSE ELISA kit (Enzyme-linked Immunosorbent Assay) was used, and the test was carried out according to the test procedure specified on the kit. To explain simply, captured antibodies were added onto 96 well plates, which were placed at 4 for one night. The 96 well plates coated with the captured antibodies were then cleaned with a cleansing buffer (PBST), and 200 μl of a diluting agent for analytic purposes (PBS with addition of 10% FBS) was added to each well before undergoing blocking for 1 hour at room temperature. After 100 μl of each standard and sample specimen was deposited onto each well and left to react for 2 hours at room temperature, another 100 μl of each detection antibody and streptavidin-HRP was deposited and left to react for 1 hour at room temperature. Next, each well was driven to develop a certain color, with the help of 100 μl of substrate solution (citric acid-phosphate buffer containing 0.01% TMB, pH 5.0, 0.001% H202), for 30 minutes at room temperature. Then, 50 μl of 2M H2S04 was added to each well in order to stop the color reaction. The level of color formation was gauged with THERMOmax, a microplate reader (Molecular Devices, U.S.A.) by measuring the absorbance at 450 nm.

Activating Inhibition of Degranulation

Activating Inhibition of Histamine and 3-Hexosaminidase Releases—Extracts of Kaladana, Cassia Seeds, Spurge, Wrinkled Giant Hyssop, Roots of Phytolaccaceae, Inner Skin of *Castanea crenata* and Rhubarbs RBL-2H3 cell strain, which is the strain type of basophils in white mice, was cultivated in the RPMI 1640 medium, which contains 10% FBS, 100 U/ml of penicillin, 100 μg/ml of streptomycin and 1.0 mM of sodium pyruvate, inside a thermo-hygrostat under the conditions of 37 and 5% CO2. It is then used to test activation of histamine and β-hexosaminidase. In order to investigate the phenomenon in which inhibition of histamine release is activated, the RBL-2H3 cell strains were deposited onto 24 well plates at 1×106 cells/ml, and kept in control overnight, stabilizing the cells. Then, 5 μl each for the aforementioned natural products (80 mg/ml) was processed in each of the wells and left to react for 1 hour. After the reaction was over, a stimulant (1 uM Calcium Ionophore A23187+50 nM PMA (Phosbol 12-Myristate 13-Acetate)) was processed and left to react for 8 hours. Then, the culture fluid was collected to run centrifugation at 5000 rpm for 5 minutes, and, subsequently, the supernatant was obtained, which was used to measure the amount of released histamine. In order to check this quantitatively, the histamine EIA (Enzyme Immunoassay) kit (EA31, Oxford, U.S.A.) was used.

That is, 50 μl of supernatant or standard specimen was added to the 96 well plates coated with monoclonal antihistamine antibodies, which was then mixed with 50 μl of an enzyme assembly. The mixture was then left at room temperature for 45 minutes and, afterwards, cleaned 3 times with a cleansing buffer. Next, 150 μl of a substrate (Tetramethyl benzidine, TMB) was also added and left to react for 15-20 minutes, after which another 50 μl of 1 N HCl was added. Any reactions were then terminated and the absorbance was measured at 450 nm.

To examine the activation of β-hexosaminidase release inhibition, 0.5 ml of RBL-2H3 cell strains were deposited onto 24 well plates at 1×10$^6$ cells/ml, while 0.5 μg/ml of mouse monoclonal IgE was added to be cultivated overnight in a thermo-hygrostat under the conditions of 37° C. and 5% CO$_2$, which resulted in the sensitization of the cells. Then, these cells were cleaned twice with 0.5 ml of siraganian buffer (119 mM NaCl, 5 mM KCl, 0.4 mM MgCl, 25 mM piperazine-N,N'-bis(2-ethanesulfonic acid) and 40 mM NaOH, pH 7.2), and added with 160 of reaction buffer (5.6 mM glucose and siraganian buffer containing 1 mM CaCl and 0.1% BSA (Bovine Serum Albumin)). The resulting solution was then cultivated at 37 for 10 minutes. Afterwards, 5 μl of kaladana, cassia seeds, spurge, wrinkled giant hyssop, roots of Phytolaccaceae, inner skin of *Castanea crenata* and rhubarbs are added to react for 20 minutes while 20 μl of DNP-HSA (Dinitrophenyl-Human Serum Albumin, 1 μg/ml) are processed as antigens and cultivated at 37 for 10 minutes in order to induce responses of allergic inflammation. After performing centrifugation on the reactant for 10 minutes at 800×g, 20 μl of supernatant and substrate (0.2 M citric acid containing 1 mM p-nitrophenyl-N-acetyl-⊕-D-glucosaminide, pH 4.5) were deposited on the 96 well plates and left to react for 1 hour at 37. To terminate the reaction, 200 μl of 0.1 M Na2CO3/NaHCO3 was added, and the amounts of chromophores and p-nitrophenols as well as the absorbance at 405 nm were measured using the ELISA reader.

Observing Modifications of Mast Cells—White Pharbitis Seeds, *Rosa multiflora* and *Nardostachys jatamanse*

After anesthetizing a mouse with ether and killing it by heavily striking the back of its head, about 10 ml of medium (pH 7.4) was injected into its abdominal cavity and the abdominal wall was gently massaged for 90 seconds before being cut at the center line. An abdominal cleansing solution was collected via a pipet and, after allowing it to undergo centrifugation at 100×g for 10 minutes, the supernatant was removed. The abdominal suspension was made and utilized in experiments in such a way that the number of mast cells becomes 1×106 cells/ml in the identical medium.

25 μl of saline or 25 μl of the white pharbitis seeds extract (1 μg/ml, 0.1 μg/ml or 0.01 μg/ml) was added to 200 μl of mast cell suspension which had been re-suspended, and was left to react for 10 minutes inside a 37-incubator. After the reaction was complete, a 25-μl solution of Compound 48/80 (Sigma Chemical Co., St. Louis, Mo., U.S.A.) was added and left to react for 20 minutes.

To observe the shape of mast cells through an optical microscope, 200 μl of the mast cell suspension in which the reaction had been completed was dropped on top of a slide glass (slide glass, 22×60 mm) located on the stage of an inverted microscope, allowing the mast cells to be precipitated and placed at room temperature for 10 minutes. By using a hemacytometer with four hundred-fold magnification, the mast cells were observed through an inverted microscope (Olympus, Japan). Being mostly round-shaped or egg-shaped, mast cells have a defined cell outline and are filled with a lot of granules inside their cytoplasm. The diameter of a mast cell is about 10-20 μm, which is twice as large as those of other cells (lymphocytes or neutrophil leukocytes) in an abdominal suspension. Thus, cells that possess these characteristics are categorized as normal mast cells. In contrast, cells that have a vague outline and/or granules within cytoplasm either sticking out of the surface or dispersed around them are regarded as degranulated type. The rate of degranulation was calculated based on the following formula.

Rate of degranulation of mast cells (%)=(the number of degranulated mast cells/the total number of mast cells)×100

Activating Inhibition Against COX Enzymes

This process was performed in "In vitro" using a modified version of the method created by Reddy and others (2000). 40 μl of enzymes (60-unit COX-1 (Cyclooxygenase) or 30-unit COX-2) for each well are added to 96 well plates while the mixture of 90 μl of 100 mM Tris-HCl buffer (pH 8.0), 20 μl of 30 μM EDTA (Ethylenediaminetetraacetic Acid), 20 μl of 150 μM hematin and 20 μl of a specimen were left to react for 5 minutes at 25. Next, another 5 μl of 5 mM TMPD and 5 μl of 20 mM arachidonic acid were added and left to react for 10 minutes at 25° C. Afterwards, the absorbance of the solution was measured at 603 nm, using the ELISA reader. For positive control groups, EGCG (Epigallocatechin Gallate, Sigma, U.S.A.) and indomethacin (Sigma, U.S.A.) were used.

Activating Inhibition Against LOX

The measurement of the activation of 15-LOX inhibition was performed in "In vitro" using the lipoxygenase inhibitor screening assay kit (Cayman, U.S.A.). 90 μl of 15-LOX (220 unit/ml) and 10 μl of 1 mM arachidonic acid were added to the 10-μl sample, and the mixture was left at room temperature for 5 minutes to react. Another 100 μl of chromogen was then added and left to react at room temperature, and the absorbance was measured at 490 nm using the ELISA reader. For positive control groups, EGCG (Epigallocatechin Gallate) and nordihydroguaiaretic acid (NDGA) were used.

Inhibiting Penetration into Epithelium

Caco-2 Cell Culture and Test for Inhibition Against Passing of OVA

Caco-2 cell strains (HTB-37) originated from ATCC underwent subculture in a MEM medium, which contains Earle's salt, 20% FBS, 1% 100 U/ml penicillin, 100 µg/mll streptomycin, 2 mM L-glutamine, 1.5 g/L sodium bicarbonate, 0.1 mM non-essential amino acid and 1.0 mM sodium pyruvate, under the conditions of 37° C. and 5% $CO_2$. In order to conduct a passing test of food allergens using a Caco-2 single cell layer, 0.5 ml of Caco-2 cells were deposited on the transmembrane, which forms the apical side of 12 transwell plates, at the concentration of $1 \times 10^5$ cells/ml by using the above culture medium (51).

On the basolateral side of a well, 1.5 ml of the culture medium was added and cultivated in a thermo-hygrostat under the conditions of 37 and 5% CO2. The medium was changed once every 2-3 days, and, in 2-3 weeks after the deposition, Caco-2 cells came to form a single cell layer. Here, the Transepitherial Electrical Resistance (TEER, $\Omega \times cm^2$) between basolateral and apical sides of the Caco-2 cells were measured using the Millicell-ERS (Electrical Resistance System, Millipore, U.S.A.), and cells whose values are greater than $300\Omega \times cm^2$ were used in experiments. The Caco-2 single cell layer was then cleaned with HBSS (Hank's Balanced Salt Solution) for 3 times, and the extracts of kaladana, cassia seeds, spurge, wrinkled giant hyssop, roots of Phytolaccaceae, inner skin of *Castanea crenata*, white pharbitis seeds, *Rosa multiflora*, *Nardostachys jatamanse* and rhubarbs (final concentration: 400 µg/ml), all of which had undergone membrane-filtration just after extracting 50% EtOH, were all added to the apical side, along with Bile salts (final concentration: 150 µg/ml). The mixture was then processed for 1 hour in a thermo-hygrostat under the conditions of 37° C. and 5% $CO_2$. Next, OVA was added to the apical side (final concentration: 400 µg/ml), and the mixture was placed in the identical thermo hygrostat with same conditions to react for 3 hours, after which the TEER value was measured one more time.

Here, succus on the basolateral side was gathered and the concentration of passed OVA was measured using sELISA. The amount of passed OVA contained within the basolateral side can be calculated as follows.

$$Flux = Cng/Hhr/Scm^2$$

In the above equation, C represents the amount of passed OVA calculated by using ELISA, H the reaction time after adding OVA in the apical side of the Caco-2 single cell layer (3 h), and S the apical side's surface area on a transwell plate (1.12 $cm^2$).

OVA Analysis by ELISA

Anti-rabbit-OVA antibodies diluted to the concentration of 2 µg/ml was combined with a coating buffer solution ((tris hydroxymethyl) aminomethane 0.05 M, pH 9.0), and 100 µl of the mixture was deposited onto 96 well plates and kept at 4 for one night. The coated 96 well plates were cleaned 3 times with a cleansing buffer solution (PBS (Phosphate Buffered Saline) containing Tween 20; PBST, 0.138 M NaCl, 0.0027 M KCl and 0.01 M phosphate buffer solution containing 0.05% Tween 20). Then, 100 µl of standard OVA, which had been diluted by a specific multiple, and the recovered solution were added to HBSS for each well, and were left to react at room temperature for 1 hour.

The well plates were cleaned again with the cleansing buffer solution, and biotin, which had been merged with anti-OVA antibodies, was diluted to a certain concentration by PBST. Then, 100 µl for each well were processed and left to react at room temperature for 1 hour. Repeating the above process with a different solution this time, the plates were cleaned with the cleansing buffer solution, avidin-HRP was diluted to a certain concentration by PBST and 100 µl of the mixture were processed for each well and left to react at room temperature for 1 hour. Then, another cleaning operation took place. Next, for a substrate solution, phenyl propionic acid or phosphate buffer (36 mM, pH 7.0) added with $H_2O$ 0.002% was used while, for a response stop solution, 100 µl of 1 M NaOH-glycine (1 M glycine/1 M NaOH) was used for each well. A fluorescent microplate reader was used to measure the fluorescence at 320/405 nm (Ex./Em. wavelength).

Treg's Induction Activity

Mouse 6- to 8-year-old female BALB/c mice were purchased from Charles River Laboratories. They were raised in an animal testing facility located at the College of Pharmacy, Seoul National University, and all tests were conducted according to the regulations and guidelines established by the Institutional Animal Care and Use Committees at Seoul National University.

Production of *Nardostachys jatamanse* Extracts

Extracts of *Nardostachys jatamanse* were provided by Korea Food Research Institute as dissolved in DMSO (Dimethyl Sulfoxide) at the concentration of 25-100 ng/ml. In order to create a concentration suitable for the experiment, the above extract was diluted by using a cell culture medium, as known as complete medium (a medium that added FBS 10%, penicillin/streptomycin 1%, sodium pyruvate 1%, non-essential amino acid 1%, HEPES 2.5% and β-mercaptoethanol 0.1% to Gibco RPMI). The same amount of DMSO, a solvent, and extract were added to a complete medium and the resulting solution was used as the control group.

Production of Cells

After putting the mouse to euthanasia with CO2, spleens and lymph nodes were separated and passed through a 70 µm strainer, which led to the acquisition of unicellular, suspended matters. In order to obtain naïve CD4 T cells, it was dyed with CD25-PE antibodies (eBioscience) and attached with anti-PE, anti-CD8α, anti-B220 and anti-CD11b bead (Miltenyl Biotec). Then, it underwent depletion using MACS (Magnetic-Activated Cell Sorting), resulting in an enrichment of CD4 T cells. Afterwards, CD62L-biotin antibodies (eBioscience) and anti-biotin bead (Miltenyl Biotec) were attached and naïve CD4 T cells were gathered through MACS. The unicellular suspended matters obtained from spleens and lymph nodes were dissolved in RBC and attached with CD3-biotin antibodies (eBioscience) and anti-biotin bead (Miltenyl Biotec) before undergoing MACS depletion. The resulting cells were used as antigen-presenting cells.

In Vitro Cell Culture

All cell culture was performed in a complete medium. In the case of antibody stimulation, 2 µg/ml of anti-CD3 was coated over 96 well flat plates throughout one night, and was added with dissolution of $5 \times 10^4$ cells/well of naïve CD4 T cells along with 1 µg/ml of anti-CD28. In the case of stimulating antigen-presenting cells, the dissolved anti-CD3 antibodies were added to the 96 well U-bottom plates, and $6 \times 10^4$ cells/well of antigen-presenting cells were cultivated with $3 \times 10^4$ cells/well of naïve CD4 T cells. In both cases, a re-combined mouse IL-2 was added with the concentration of 10 ng/ml, and the extract diluted to a desired concentration was then added to each well. These were cultivated under the conditions of 37° C. and 5% $CO_2$ for 72 hours before the cells were collected and analyzed.

Foxp3 Dyeing in Cells and Cell Migration Analysis

The cultivated cells were withdrawn and dyed on the surface for 15 minutes by using a buffer solution, a mixture of PBSN (0.14M NaCl, 0.003M KCl, 0.01M $Na_2HPO_4$, 0.002M $KHPO_4$, 0.002M $NaN_3$) and 1% FBS, and CD4-PE/Cy7 (Biolegend). Afterwards, eBioscience's Foxp3 dye set was used to stain Foxp3 in cells, according to specified instructions. For the FACS analysis, BD FACS Calibur and Cell Questpro were used.

Statistical Processing

Results of all experiments were displayed with average values and standard deviation, and the difference between each group and its specimen was verified within the significant difference of $p<0.05$ through ANOVA, which uses SAS, and Duncan's multiple range test.

Results

Activating Inhibition of IL-4 Production

As specified in "Test Procedure & Materials", a test was conducted to check the activation of IL-4 production inhibition in spleen cells induced by several natural products, which are kaladana, cassia seeds, spurge, wrinkled giant hyssop, roots of Phytolaccaceae, inner skin of *Castanea crenata*, white pharbitis seeds, *Rosa multiflora*, *Nardostachys jatamanse* or rhubarbs. The concentration of the above extracts were 4 μl/ml (about 80 ng/ml), and the results of activating inhibition on IL-4 production, compared to the control group, are shown in Table 1.

TABLE 1

| Specimen | Levels of IL-4 inhibition (%) |
| --- | --- |
| Kaladana | 94.0 ± 3.3 |
| Cassia seeds | 0 |
| Spurge | 30.0 ± 6.0 |
| Rhubarbs | 81.8 ± 5.0 |
| Wrinkled giant hyssop | 70.0 ± 18.2 |
| Roots of Phytolaccaceae | 57.2 ± 22.2 |
| Inner skin of *Castanea crenata* | 27.9 ± 2.2 |

These results show that the extracts of spurge, rhubarb, giant hyssop, roots of Phytolaccaceae and inner skin of *Castanea crenata* have inhibitive effects of greater than 30% against the production of IL-4, and rhubarb and giant hyssop extracts have effects greater than 70% while the kaladana extracts have greater than 90% inhibitive effects.

The IC50 value of kaladana extracts, which have a high activation level of IL-4 inhibition, is 7.4 μg/ml, and that of wrinkled giant hyssop extracts is 30.91 μg/ml while that of the Phytolaccaceae roots is 1.95 μg/ml.

Figure 2:
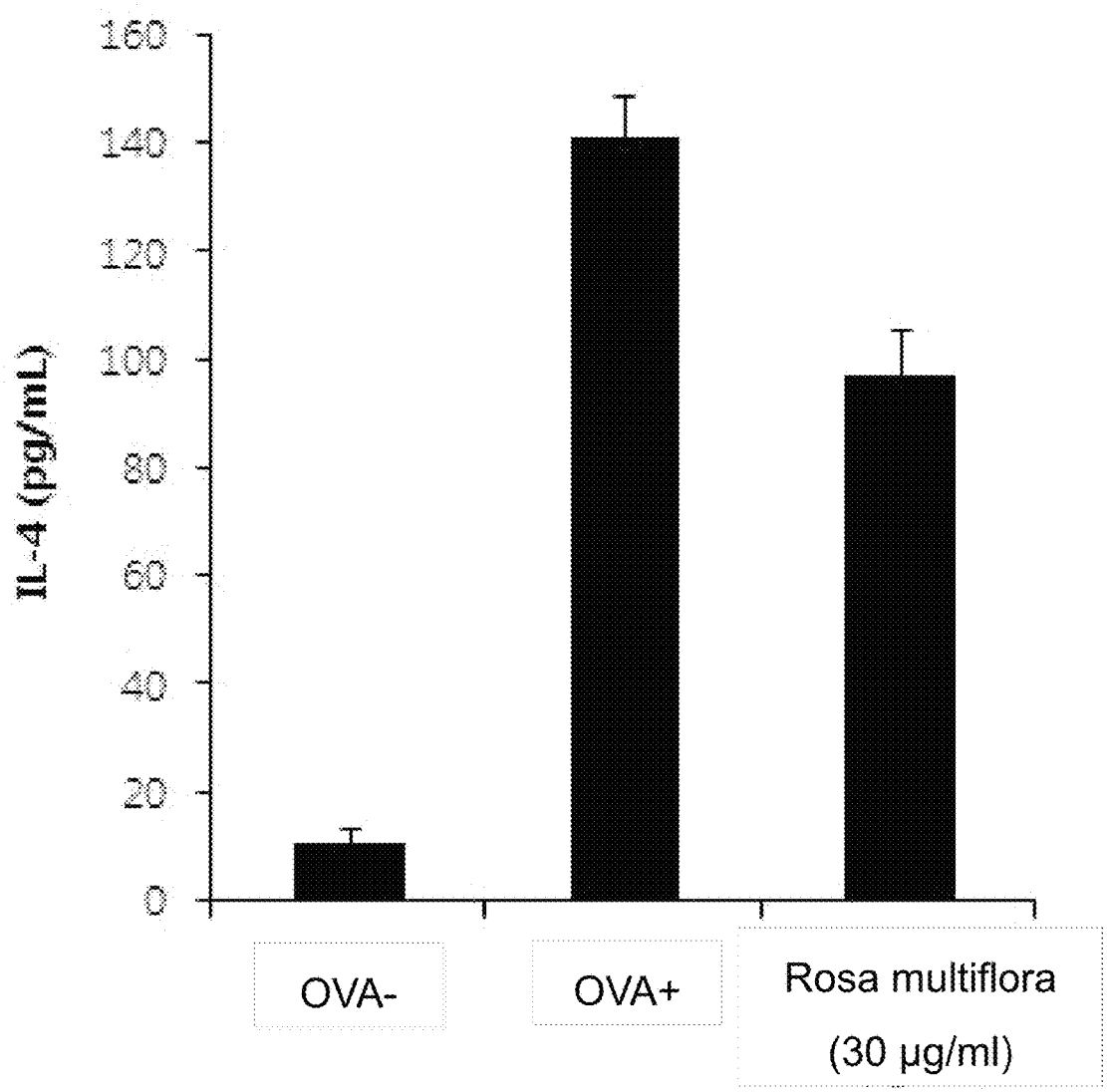
FIG. 2 displays the effect of *Rosa multiflora* extracts in releasing IL-4 of mouse splenocytes.
Figure 3:
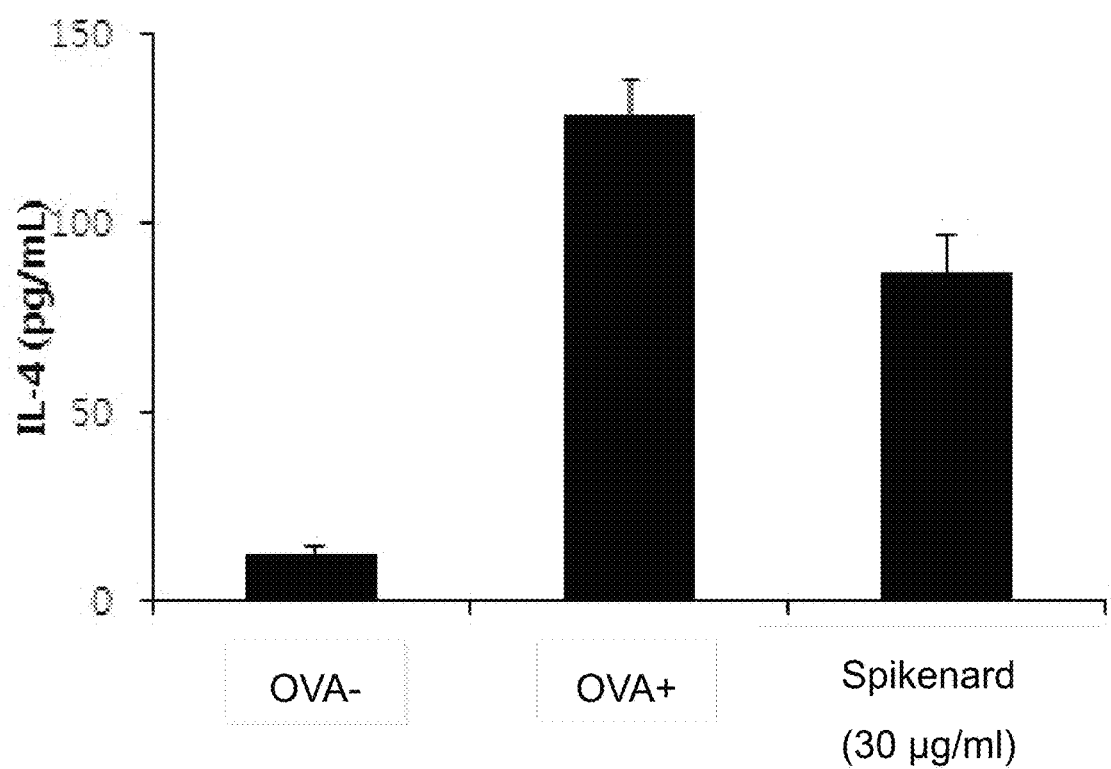
FIG. 3 displays the effect of *Nardostachys jatamanse* extracts in creating IL-4 of mouse splenocytes.

An investigation of the effects that white pharbitis seeds have on spleen cells' IL-4 production shows that the white pharbitis seed extracts reduced the IL-4 production in spleen cells by about 60% at the concentration of 10 μl/ml, compared to the control group (FIG. 1). Also, the extracts of *rosa multiflora* reduced the IL-4 production in spleen cells by about 30% at the concentration of 30 μl/ml, compared to the control group (FIG. 2). Lastly, the extracts of *nardostachys jatamanse* reduced the IL-4 production in spleen cells by about 35% at the concentration of 30 μl/ml, compared to the control group (FIG. 3).

Activating Inhibition of Histamine Release

The inhibition of histamine release activated by kaladana, cassia seeds, spurge, wrinkled giant hyssop, roots of Phytolaccaceae, inner skin of *Castanea crenata*, white pharbitis seeds, *Rosa multiflora, Nardostachys jatamanse* or rhubarbs was examined. The amount of histamine released without any processing conducted is 167.7 ng/ml, and if only a stimulant (Calcium Ionophore A23187 and PMA (Phosbol 12-Myristate 13-Acetate)) is processed, the amount of histamine released is 232.4 ng/ml. The inhibition rate of histamine release was calculated using the following formula.

[(amount of histamine release when processing stimulants only)−(amount of histamine release when processing kaladana extracts and stimulants)]/[(amount of histamine release when processing stimulants only)−(amount of histamine release without any processing)]×100=rate of inhibition (%)

Table 2 shows the inhibition rates calculated from the histamine released due to processing of the extracts. "Amount of Histamine Released" in the table is a value which subtracts the amount of histamine released without any processing (167.7 ng/ml) from the total amount when the extracts perform processing.

TABLE 2

| Specimen | Amount of Histamine Released | Rate of Inhibition (%) |
| --- | --- | --- |
| Kaladana | 180.9 ± 1.2 | 80.4 ± 7.0 |
| Cassia seeds | 220.5 ± 5.1 | 26.0 ± 2.5 |
| Spurge | 203.1 ± 2.2 | 49.9 ± 3.0 |
| Rhubarbs | 218.3 ± 8.7 | 29.0 ± 4.9 |
| Wrinkled giant hyssop | 211.4 ± 3.4 | 38.5 ± 3.0 |
| Roots of Phytolaccaeae | 187.0 ± 1.7 | 72.2 ± 6.0 |
| Inner skin of *Castanea crenata* | 214.6 ± 4.2 | 34.2 ± 3.0 |

When processing the kaladana extracts, the amount of histamine released came out to be 180.9±1.2 ng/ml, and the rate of inhibition against histamine release was 80.4±7.0%, the highest of all. All extracts showed good activation of inhibition against histamine release.

Activating Inhibition of β-Hexosaminidase Release

The inhibition of β-hexosaminidase release activated by the extracts of kaladana, cassia seeds, spurge, rhubarbs, wrinkled giant hyssop, roots of Phytolaccaceae and inner skin of *Castanea crenata* was examined. Without any processing, the A405 absorbance, which represents the degree of β-hexosaminidase release, is 0.121, and if only stimulants (anti-DNP (Dinitrophenyl) IgE antibody and DNP-HAS (Dinitrophenyl-Human Serum Albumin)) are processed, the A405 absorbance is 0.390. The inhibition rate of β-hexosaminidase release is calculated by the following formula.

[($A405$ when processing stimulants only)−($A405$ when processing kaladana extracts and stimulants)]/[($A405$ when processing stimulants only)−($A405$ without any processing)]−100=rate of inhibition (%)

Table 3 shows the rates of inhibition calculated from β-hexosaminidase released due to processing of the extracts.

TABLE 3

| Specimen | OD value (A405) | Rate of Inhibition (%) |
|---|---|---|
| Kaladana | 0.149 ± 0.01 | 44.6 ± 1.8% |
| Cassia seeds | 0.165 ± 0.02 | 38.6 ± 1.5 |
| Spurge | 0.144 ± 0.02 | 46.5 ± 5.5 |
| Rhubarbs | 0.223 ± 0.08 | 17.2 ± 7.2 |
| Wrinkled giant hyssop | 0.178 ± 0.02 | 33.7 ± 4.2 |
| Roots of Phytolaccaceae | 0.137 ± 0.01 | 49.2 ± 2.0 |
| Inner skin of Castanea crenata | 0.202 ± 0.02 | 24.8 ± 2.8 |

When processing Phytolaccaceae root extracts, the A405 absorbance, which shows the amount of β-hexosaminidase release, came out to be 0.137±0.01, and the rate of β-hexosaminidase release inhibition was 49.2±2.0%, the highest among all. All extracts showed good activation of inhibition against β-hexosaminidase release.

Table 4 shows the inhibition rates of histamine and β-hexosaminidase releases for each of the extracts.

TABLE 4

| Specimen | Rate of Inhibition against Histamine Release (%) | Rate of Inhibition against β-hexosaminidase Release (%) |
|---|---|---|
| Kaladana | 80.4 ± 7.0 | 44.6 ± 1.8% |
| Cassia seeds | 26.0 ± 2.5 | 38.6 ± 1.5 |
| Spurge | 49.9 ± 3.0 | 46.5 ± 5.5 |
| Rhubarbs | 29.0 ± 4.9 | 17.2 ± 7.2 |
| Wrinkled giant hyssop | 38.5 ± 3.0 | 33.7 ± 4.2 |
| Roots of Phytolaccaceae | 72.2 ± 6.0 | 49.2 ± 2.0 |
| Inner skin of Castanea crenata | 34.2 ± 3.0 | 24.8 ± 2.8 |

Modifications of Mast Cells

Figure 4:
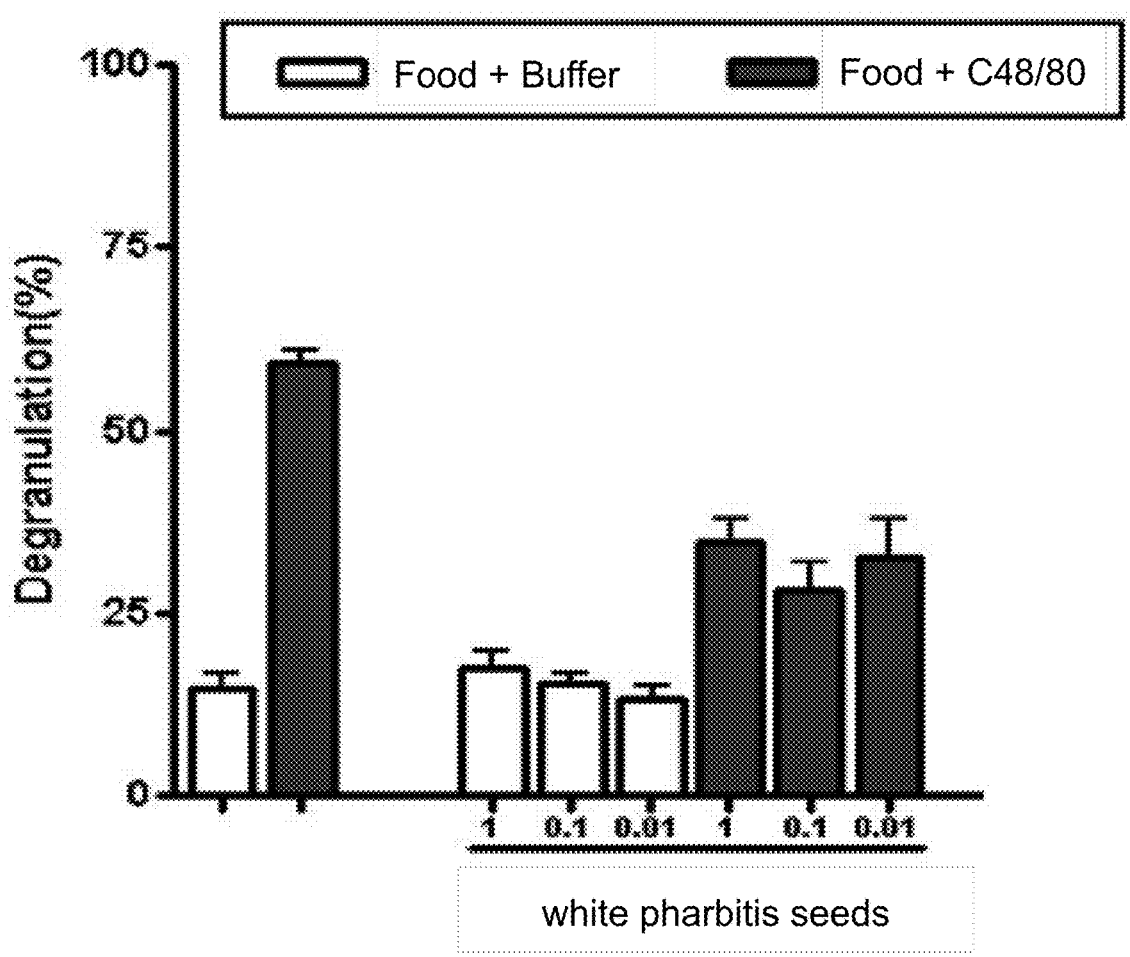
FIG. 4 displays the effect of white pharbitis seed extracts in degranulation of mouse mast cells.
Figure 5:
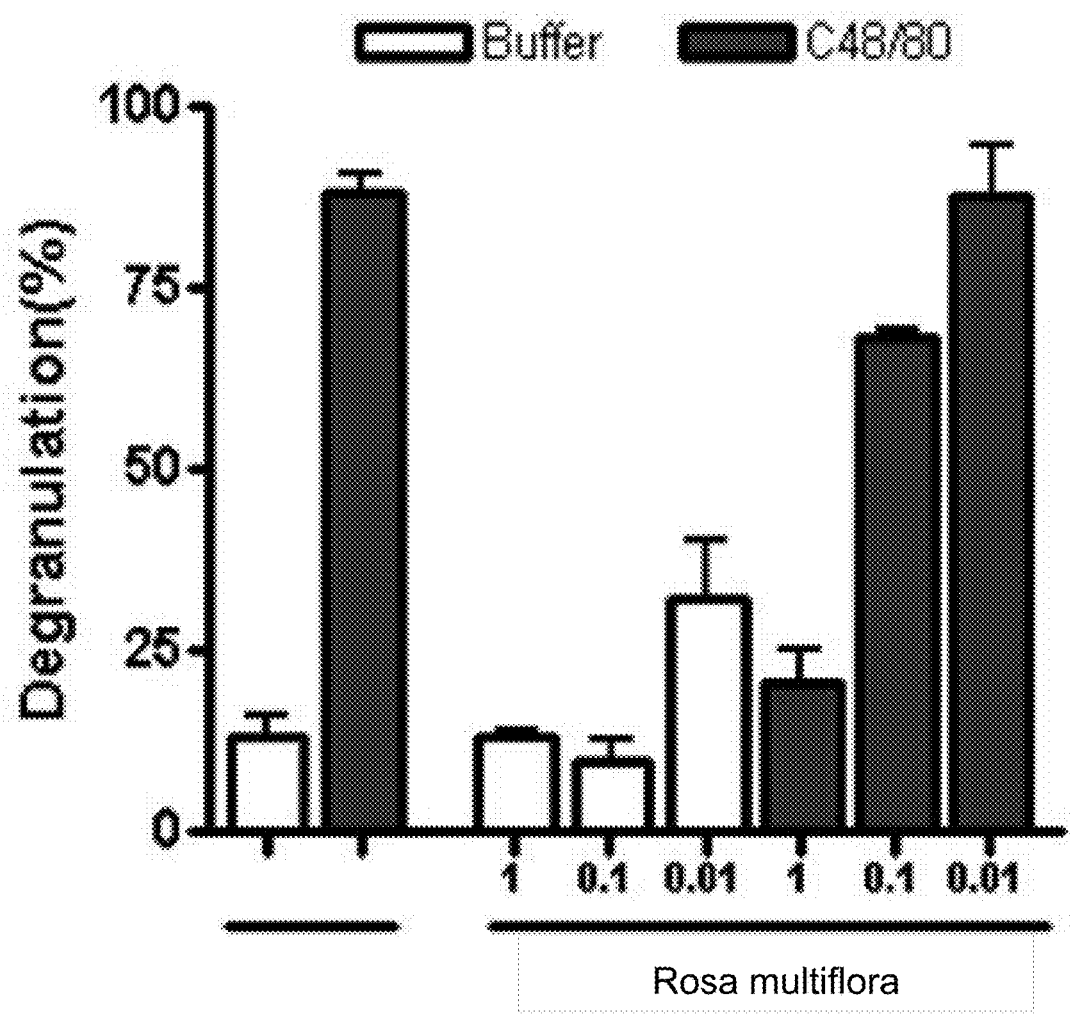
FIG. 5 displays the effect of *Rosa multiflora* extracts in degranulation of mouse mast cells.
Figure 6:
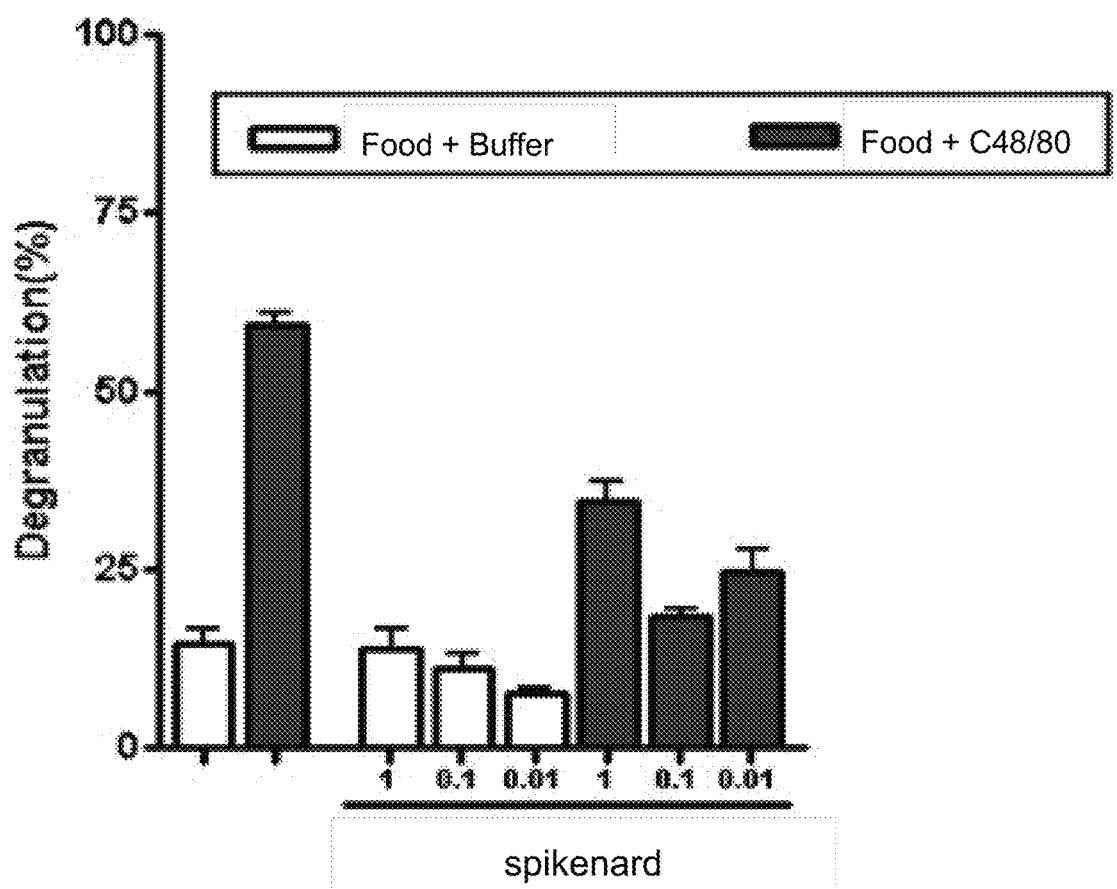
FIG. 6 displays the effect of *Nardostachys jatamanse* extracts in degranulation of mouse mast cells.
Figure 7:
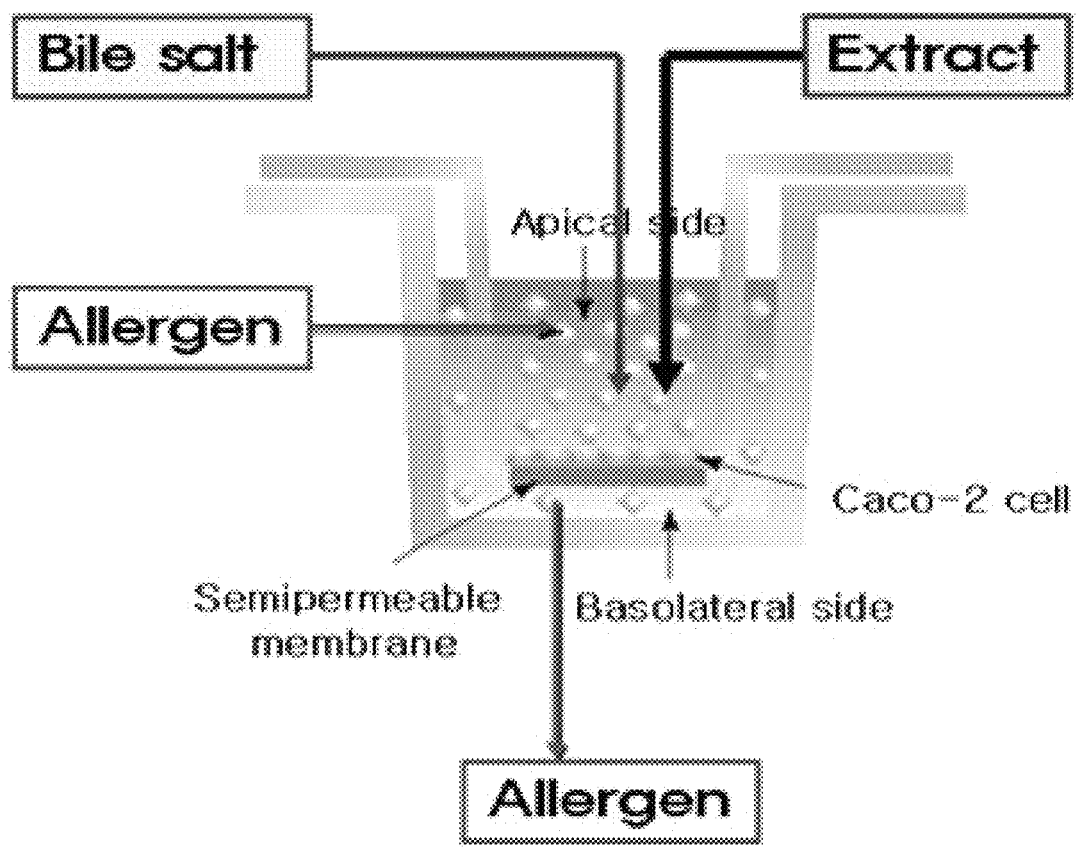
FIG. 7 displays a diagram of the test on allergens' penetration into epithelial cells.
Figure 8:
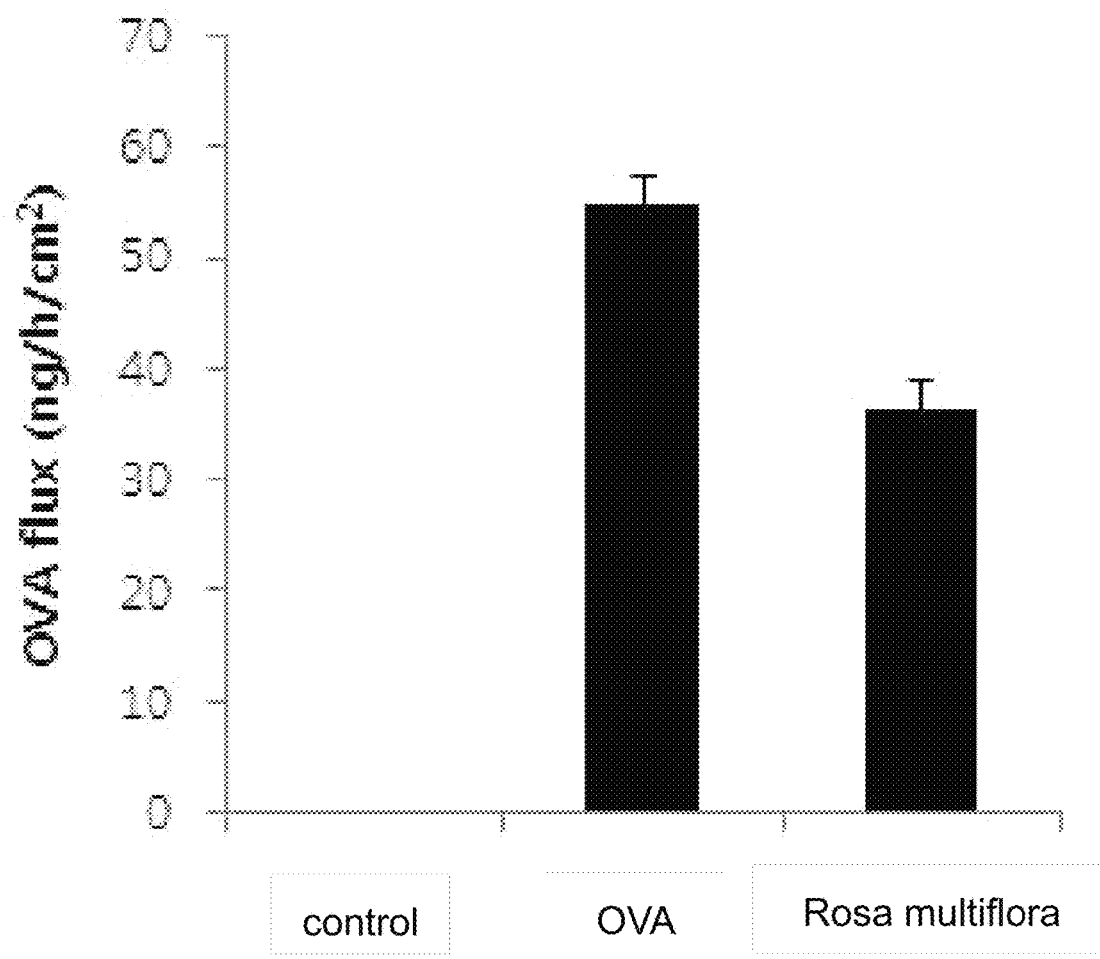
FIG. 8 displays the effect of *Rosa multiflora* extracts in allergens' penetration into epithelial cells.

The effects that white pharbitis seeds, *rosa multiflora* and *nardostachys jatamanse* extracts have on the degranulation rate of mast cells due to Compound 48/80 were examined. Compared to the control group that only processed Compound 48/80, adding 0.01, 0.1 and 1.0 µg/ml of white pharbitis seed extract to a test group that had been processed with Compound 48/80 turned out to show effects of degranulation inhibition by 40-60%. Similarly, if 0.1 and 1.0 µg/ml of *rosa multiflora* extracts is processed, the effect of degranulation inhibition was about 22% and 80%, respectively. Lastly, if 0.01, 0.1 and 1.0 µg/ml of *nardostachys jatamanse* extracts are processed, the effect of degranulation inhibition was between 50 and 70% (FIGS. 3-5).

Activating In Vitro Inhibition Against COX-1 and COX-2 Enzymes

Mast cells are essential elements involved in the electric reaction, which is the second stage of an allergic crisis. Once phospholipid metabolism becomes active due to the enzymes in mast cells, the metabolites further intensify the allergic responses (allergic inflammatory reaction). Therefore, to help alleviate and suppress allergies, the presence of activities that hinder the effect of COX (Cyclooxygenase, especially COX-2) within the extracts of the aforementioned natural products was to be investigated.

It was determined that the extracts that have high activated inhibition against COX-2, which is closely related to inflammatory reaction, but have low activated inhibition against COX-1, normally an essential enzyme in a body, were to be selected. The absorbance value of the control group that displays activation of COX-1 was 0.173, and, in case the kaladana extracts were processed, the value was 0.139 (COX-1 activation) and 0.123 (COX-2 activation). Such extracts are expected to help suppress the electric reaction, the second stage of allergic crises.

Table 5 shows activation of inhibition against COX-1 and COX-2 for each type of extracts.

TABLE 5

| Specimen | Activation of Inhibition against COX-1 (A603) | Activation of Inhibition against COX-2 (A603) |
|---|---|---|
| Kaladana | 0.13 | 0.123 |
| Cassia seeds | 0.492 | −0.001 |
| Spurge | 0.198 | 0.012 |
| Rhubarbs | 0.138 | −0.002 |
| Wrinkled giant hyssop | 0.189 | 0.126 |
| Roots of Phytolaccaceae | 0.122 | 0.159 |
| Inner skin of Castanea crenata | 0.162 | 0.008 |

Among these, extracts with outstanding activation of inhibition against COX-2 (cassia seeds, spurges and inner skin of *Castanea crenata*) were chosen to compare their IC50 values.

TABLE 6

| Specimen | COX-1 IC50(µg/ml) | COX-2 IC50(µg/ml) | COX-1 IC50/COX-2 IC50 |
|---|---|---|---|
| Cassia seeds | 65 | 200 | 3.08 |
| Spurge | 10.9 | 39 | 3.58 |
| Inner skin of Castanea crenata | 4.1 | 35 | 8.54 |

In Table 6, the cassia seed extracts are believed to have the most superb activation of inhibition since they have the smallest ratio of COX-1 IC50 value to COX-2 IC50 value. However, more important than a small ratio is a low COX-2 IC50 value.

Activating Inhibition Against LOX

Besides COX, LOX (Lipoxygenase) also produces phospholipid metabolites by being involved in the electric reaction, which is the second stage of an allergic crisis, and leads to induce inflammation. That is, reducing LOX will help in alleviating the symptoms. Therefore, the presence of activities that hinder the effect of 15-LOX, one of its enzymes, within the extracts of the aforementioned natural products was to be investigated.

From the study of the activation of 15-LOX inhibition by various extracts, spurge and Phytolaccaceae root extracts showed outstanding IC50 values, which are 87 and 100 µg/ml, respectively.

Inhibiting Penetration into Epithelium

Food allergic crises occur as undigested allergens pass through the layer of intestinal epithelial cells and are absorbed into the body, which subsequently results in hypersensitive immune responses. Thus, if the activating materials that can suppress the allergens' passage through the small intestine are explored, selected and utilized, it may be possible to control food allergic crises. Based on this theory, this invention has investigated the activation of cassia seeds, spurge, wrinkled giant hyssop, Phytolaccaceae roots or *Nardostachys jatamanse* extracts to inhibit penetration through the layer of intestinal epithelial cells. In conclusion, the cassia seed extracts show the most outstanding performance by only allowing about 6% of allergens to pass through epithelium.

Also, when *rosa multiflora* extracts are processed, the amount of OVA penetration was found to be reduced, compared to the positive control group that only processed OVA without any extracts. Converting this result to percentages, the processing of *rosa multiflora* extracts reduces the passage rate of allergens by 30-50%.

Foxp3 Dyeing in Cells and Cell Migration Analysis

Figure 9A:
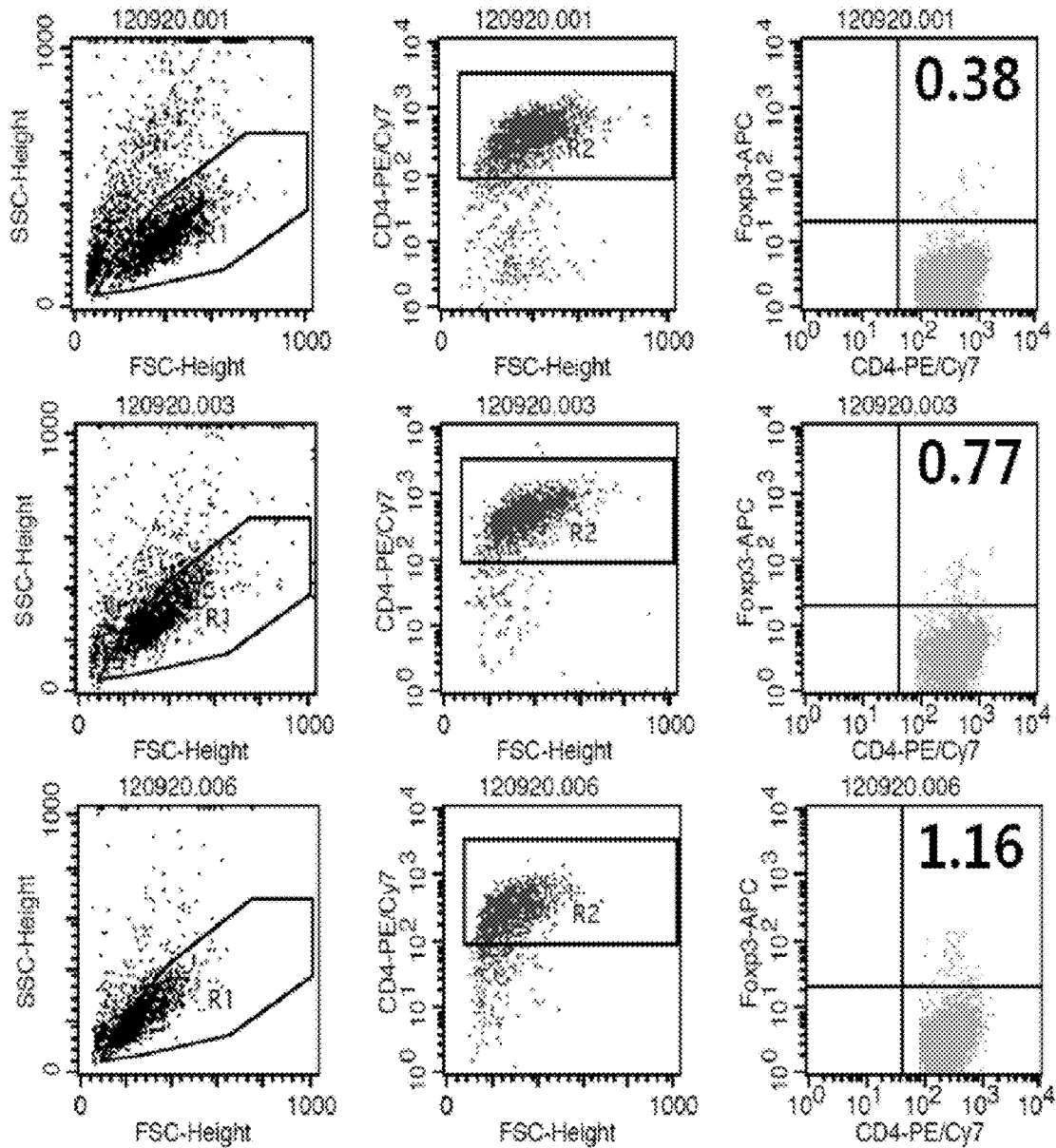
FIGS. 9a and 9b display the effect of *Nardostachys jatamanse* extracts in the induction of mouse splenocytes and lymph node cells into Treg cells.
Figure 9B:
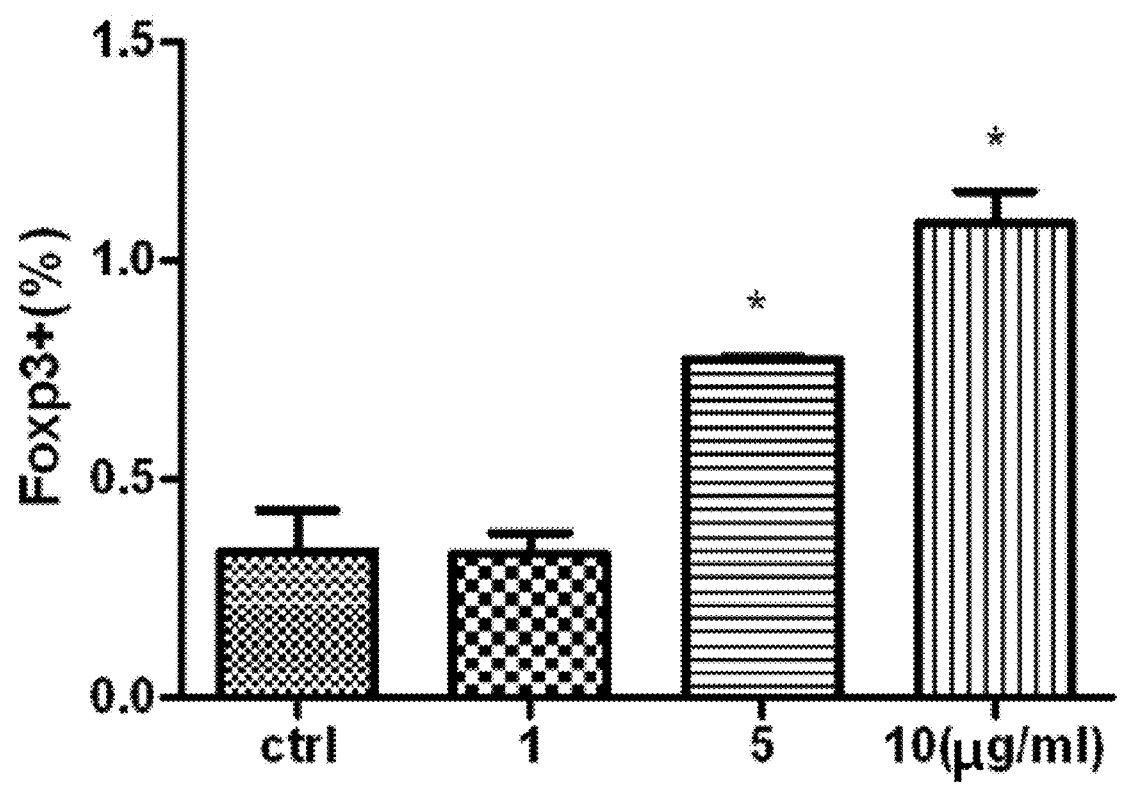

It has been found that the concentration-dependent characteristic of *Nardostachys jatamanse* extracts increases the manifestation of Foxp3 in cells (FIG. 9). In other words, it means that the *Nardostachys jatamanse* extracts also increase the number of Treg cells.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method of improving or treating an allergic disease comprising: administering a composition comprising an extract of fruits of *Rosa multiflora* (*Rosa multiflora*) in a therapeutically effective amount to a subject in need thereof, wherein the extract of *Rosa multiflora* inhibits the degranulation of mast cells.

2. The method of claim 1, wherein the allergic disease is asthma, allergic rhinitis, allergic dermatitis, allergic atopic dermatitis, or a food allergy.

3. The method of claim 1, wherein the extract inhibits the production of IL-4.

* * * * *